(12) United States Patent
Yang et al.

(10) Patent No.: US 12,135,332 B2
(45) Date of Patent: Nov. 5, 2024

(54) MUTANT HUMAN ESTROGEN RECEPTOR-α AND METHODS OF USE THEREOF

(71) Applicant: Case Western Reserve University, Cleveland, OH (US)

(72) Inventors: Sichun Yang, Solon, OH (US); Yi Peng, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 1196 days.

(21) Appl. No.: 16/695,487

(22) Filed: Nov. 26, 2019

(65) Prior Publication Data

US 2020/0166530 A1    May 28, 2020

Related U.S. Application Data

(60) Provisional application No. 62/893,856, filed on Aug. 30, 2019, provisional application No. 62/772,296, filed on Nov. 28, 2018.

(51) Int. Cl.
| | |
|---|---|
| C07K 14/47 | (2006.01) |
| C07K 14/525 | (2006.01) |
| G01N 33/566 | (2006.01) |
| G01N 33/574 | (2006.01) |
| G01N 33/94 | (2006.01) |

(52) U.S. Cl.
CPC ......... *G01N 33/94* (2013.01); *C07K 14/4748* (2013.01); *C07K 14/525* (2013.01); *G01N 33/566* (2013.01); *G01N 33/5748* (2013.01); *G01N 2500/04* (2013.01); *G01N 2500/20* (2013.01)

(58) Field of Classification Search
CPC .. G01N 33/94; G01N 33/566; G01N 33/5748; G01N 2500/04; G01N 2500/20; G01N 33/743; G01N 2333/723; C07K 14/4748; C07K 14/525; C07K 14/721
See application file for complete search history.

(56) References Cited

PUBLICATIONS

Vickery, Larry E. Structure/Function of Recombinant Human Estrogen Receptor. California Univ Irvine, 1998 (Year: 1998).*
Carlson et al. Altered Ligand Binding Properties and Enhanced Stability of a Constitutively Active Estrogen Receptor: Evidence That an Open Pocket Conformation Is Required for Ligand Interaction. Biochemistry 1997, 36, 14897-14905 (Year: 1997).*
Luck et al. 2000.Conformational Changes in the Human Estrogen Receptor Observed by 19F NMR. Biochemical and Biophysical Research Communications 270, 988-991 (Year: 2000).*
Huang et al. 2018 Multidomain architecture of estrogen receptor reveals interfacial cross-talk between its DNA binding and ligand-binding domains. Nature Communications 9:3520 (Year: 2018).*
Xiang, Zhexin, Cinque S. Soto, and Barry Honig. "Evaluating conformational free energies: the colony energy and its application to the problem of loop prediction." Proceedings of the National Academy of Sciences 99.11 (2002): 7432-7437.
Case, David A., et al. "The Amber biomolecular simulation programs." Journal of computational chemistry 26.16 (2005): 1668-1688.
Maier, James A., et al. "ff14SB: improving the accuracy of protein side chain and backbone parameters from ff99SB." Journal of chemical theory and computation 11.8 (2015): 3696-3713.
Price, Daniel J., and Charles L. Brooks III. "A modified TIP3P water potential for simulation with Ewald summation." The Journal of chemical physics 121.20 (2004): 10096-10103.
Zgarbova, Marie, et al. "Toward improved description of DNA backbone: revisiting epsilon and zeta torsion force field parameters." Journal of chemical theory and computation 9.5 (2013): 2339-2354.
Wang, Junmei, et al. "Development and testing of a general amber force field." Journal of computational chemistry 25.9 (2004): 1157-1174.
Valentini, Erica, et al. "SASBDB, a repository for biological small-angle scattering data." Nucleic acids research 43. D1 (2015): D357-D363.
Huang, Wei, et al. "Multidomain architecture of estrogen receptor reveals interfacial cross-talk between its DNA-binding and ligand-binding domains." Nature communications 9.1 (2018): 1-10.
McDonnell, Donald P. "Neomorphic ERa Mutations Drive Progression in Breast Cancer and Present a Challenge for New Drug Discovery", Cancer Cell, vol. 33, Issue 2 Feb. 12, 2018 pp. 153-336.
Kumar, Vijay, et al. "Functional domains of the human estrogen receptor." Cell 51.6 (1987): 941-951.
Deroo, Bonnie J., and Kenneth S. Korach. "Estrogen receptors and human disease." The Journal of clinical Investigation 116.3 (2006): 561-570.
Kumar, Vijay, and Pierre Chambon. "The estrogen receptor binds tightly to its responsive element as a ligand-induced homodimer." Cell 55.1 (1988): 145-156.
Dahlman-Wright, Karin, et al. "International union of pharmacology. LXIV. Estrogen receptors." Pharmacological reviews 58.4 (2006): 773-781.
Chandra, Vikas, et al. "Structure of the intact PPAR-?-RXR-a nuclear receptor complex on DNA." Nature 456.7220 (2008): 350-356.
Zhang, Jun, et al. "DNA binding alters coactivator interaction surfaces of the intact VDR-RXR complex." Nature structural & molecular biology 18.5 (2011): 556.

(Continued)

*Primary Examiner* — Celine X Qian
*Assistant Examiner* — Tiffany Nicole Grooms
(74) *Attorney, Agent, or Firm* — Tarolli, Sundheim, Covell & Tummino LLP

(57) ABSTRACT

One aspect of the present disclosure relates to an isolated mutant human estrogen receptor alpha (hERα) that may be used in methods of drug discovery. The isolated mutant hERα can include a DNA-binding domain (DBD), a ligand-binding domain (LBD), and an interface between the DBD and the LBD, wherein at least one tryptophan residue is mutated to a phenylalanine residue.

10 Claims, 16 Drawing Sheets
Specification includes a Sequence Listing.

(56) References Cited

PUBLICATIONS

Rochel, Natacha, et al. "Common architecture of nuclear receptor heterodimers on DNA direct repeat elements with different spacings." Nature structural & molecular biology 18.5 (2011): 564.

Chandra, Vikas, et al. "Multidomain integration in the structure of the HNF-4a nuclear receptor complex." Nature 495.7441 (2013): 394-398.

Lou, Xiaohua, et al. "Structure of the retinoid X receptor a-liver X receptor β (RXRa-LXRβ) heterodimer on DNA." Nature structural & molecular biology 21.3 (2014): 277-281.

Maletta, Massimiliano, et al. "The palindromic DNA-bound USP/EcR nuclear receptor adopts an asymmetric organization with allosteric domain positioning." Nature communications 5.1 (2014): 1-7.

Chandra V, Wu D, Li S, Potluri N, Kim Y, Rastinejad F. The quaternary architecture of RARβ-RXRa heterodimer facilitates domain-domain signal transmission. Nat Commun. Oct. 11, 2017;8(1):868. doi: 10.1038/s41467-017-00981-y. PMID: 29021580; PMCID: PMC5636793.

Schwabe, John WR, et al. "The crystal structure of the estrogen receptor DNA-binding domain bound to DNA: how receptors discriminate between their response elements." Cell 75.3 (1993): 567-578.

Shiau, Andrew K., et al. "Structural characterization of a subtype-selective ligand reveals a novel mode of estrogen receptor antagonism." Nature structural biology 9.5 (2002): 359-364.

Warnmark, Anette, et al. "Interaction of transcriptional intermediary factor 2 nuclear receptor box peptides with the coactivator binding site of estrogen receptor a." Journal of Biological Chemistry 277.24 (2002): 21862-21868.

Gangloff, Monique, et al. "Crystal structure of a mutant hERa ligand-binding domain reveals key structural features for the mechanism of partial agonism." Journal of Biological Chemistry 276.18 (2001): 15059-15065.

Tanenbaum, David M., et al. "Crystallographic comparison of the estrogen and progesterone receptor's ligand binding domains." Proceedings of the National Academy of Sciences 95.11 (1998): 5998-6003.

Yi, Ping, et al. "Structural and functional impacts of ER coactivator sequential recruitment." Molecular cell 67.5 (2017): 733-743.

Yi, Ping, et al. "Structure of a biologically active estrogen receptor-coactivator complex on DNA." Molecular cell 57.6 (2015): 1047-1058.

Huang, Wei, et al. "Cross-talk between the ligand-and DNA-binding domains of estrogen receptor." Proteins: Structure, Function, and Bioinformatics 81.11 (2013): 1900-1909.

Takamoto, Keiji, and Mark R. Chance. "Radiolytic protein footprinting with mass spectrometry to probe the structure of macromolecular complexes." Annu. Rev. Biophys. Biomol. Struct. 35 (2006): 251-276.

Wang, Liwen, and Mark R. Chance. "Protein footprinting comes of age: mass spectrometry for biophysical structure assessment." Molecular & Cellular Proteomics 16.5 (2017): 706-716.

Huang, Wei, et al. "Quantitative mapping of protein structure by hydroxyl radical footprinting-mediated structural mass spectrometry: a protection factor analysis." Biophysical journal 108.1 (2015): 107-115.

Kaur, Parminder, et al. "Quantitative protein topography analysis and high-resolution structure prediction using hydroxyl radical labeling and tandem-ion mass spectrometry (MS)." Molecular & Cellular Proteomics 14.4 (2015): 1159-1168.

Graewert, Melissa A., and Dmitri I. Svergun. "Impact and progress in small and wide angle X-ray scattering (SAXS and WAXS)." Current opinion in structural biology 23.5 (2013): 748-754.

Bernado, Pau, and Martin Blackledge. "Proteins in dynamic equilibrium." Nature 468.7327 (2010): 1046-1048.

Rambo, Robert P., and John A. Tainer. "Super-resolution in solution X-ray scattering and its applications to structural systems biology." Annual review of biophysics 42 (2013): 415-441.

Yang, Sichun. "Methods for SAXS-based structure determination of biomolecular complexes." Advanced materials 26.46 (2014): 7902-7910.

Yang, Sichun, et al. "Multidomain assembled states of Hck tyrosine kinase in solution." Proceedings of the National Academy of Sciences 107.36 (2010): 15757-15762.

Huang, Wei, et al. "Theoretical modeling of multiprotein complexes by iSPOT: Integration of small-angle X-ray scattering, hydroxyl radical footprinting, and computational docking." Journal of structural biology 196.3 (2016): 340-349.

Hisieh, An, et al. "A practical guide to iSPOT modeling: an integrative structural biology platform." Biological Small Angle Scattering: Techniques, Strategies and Tips. Springer, Singapore, 2017. 229-238.

Webb, Benjamin, et al. "Integrative structure modeling with the Integrative Modeling Platform." Protein Science 27.1 (2018): 245-258.

Van Zundert, G. C. P., et al. "The HADDOCK2. 2 web server: user-friendly integrative modeling of biomolecular complexes." Journal of molecular biology 428.4 (2016): 720-725.

Grishaev, Alexander, et al. "Refined solution structure of the 82-kDa enzyme malate synthase G from joint NMR and synchrotron SAXS restraints." Journal of biomolecular NMR 40.2 (2008): 95-106.

Sterckx, Yann GJ, et al. "Small-angle X-ray scattering-and nuclear magnetic resonance-derived conformational ensemble of the highly flexible antitoxin PaaA2." Structure 22.6 (2014): 854-865.

Ravikumar, Krishnakumar M., Wei Huang, and Sichun Yang. "Fast-SAXS-pro: a unified approach to computing SAXS profiles of DNA, RNA, protein, and their complexes." The Journal of chemical physics 138.2 (2013): 01B609.

Svergun, D. I. B. C., Claudio Barberato, and Michel HJ Koch. "CRYSOL—a program to evaluate X-ray solution scattering of biological macromolecules from atomic coordinates." Journal of applied crystallography 28.6 (1995): 768-773.

Sobolev, Vladimir, et al. "Automated analysis of interatomic contacts in proteins." Bioinformatics (Oxford, England) 15.4 (1999): 327-332.

Zehir, Ahmet, et al. "Mutational landscape of metastatic cancer revealed from prospective clinical sequencing of 10,000 patients." Nature medicine 23.6 (2017): 703.

Cancer Genome Atlas Research Network. "Comprehensive genomic characterization of squamous cell lung cancers." Nature 489.7417 (2012): 519.

Giannakis, Marios, et al. "Genomic correlates of immune-cell infiltrates in colorectal carcinoma." Cell reports 15.4 (2016): 857-865.

Levine, Douglas A., and Cancer Genome Atlas Research Network. "Integrated genomic characterization of endometrial carcinoma." Nature 497.7447 (2013): 67-73.

Gao, Jianjiong, et al. "Integrative analysis of complex cancer genomics and clinical profiles using the cBioPortal." Science signaling 6.269 (2013): p. l1-p. l1.

Wells, James A., and Christopher L. McClendon. "Reaching for high-hanging fruit in drug discovery at protein-protein interfaces." Nature 450.7172 (2007): 1001-1009.

Seiler, Catherine Y., et al. "DNASU plasmid and PSI: Biology-Materials repositories: resources to accelerate biological research." Nucleic acids research 42.D1 (2014): D1253-D1260.

Stols, Lucy, et al. "A new vector for high-throughput, ligation-independent cloning encoding a tobacco etch virus protease cleavage site." Protein expression and purification 25.1 (2002): 8-15.

Xu, Hua, and Michael A. Freitas. "A mass accuracy sensitive probability based scoring algorithm for database searching of tandem mass spectrometry data." BMC bioinformatics 8.1 (2007): 133.

Trewhella, Jill, et al. "2017 publication guidelines for structural modelling of small-angle scattering data from biomolecules in solution: an update." Acta Crystallographica Section D: Structural Biology 73.9 (2017): 710-728.

Anami, Yasuaki, et al. "Apo-and antagonist-binding structures of vitamin D receptor ligand-binding domain revealed by hybrid

(56) References Cited

PUBLICATIONS approach combining small-angle X-ray scattering and molecular dynamics." Journal of Medicinal Chemistry 59.17 (2016): 7888-7900.

* cited by examiner

MTMTLHTKASGMALLHQIQGNELEPLNRPQLKIPLERPLGEVYLDSSKPAVYNYPEGAAY
EFNAAAAANAQVYGQTGLPYGPGSEAAAFGSNGLGGFPPLNSVSPSPLMLLHPPPQLSPF
LQPHGQQVPYYLENEPSGYTVREAGPPAFYRPNSDNRRQGGRERLASTNDKGSMAMESAK
ETRYCAVCNDYASGYHYGVWSCEGCKAFFKRSIQGHNDYMCPATNQCTIDKNRRKSCQAC
RLRKCYEVGMMKGGIRKDRRGGRMLKHKRQRDDGEGRGEVGSAGDMRAANLWPSPLMIKR
SKKNSLALSLTADQMVSALLDAEPPILYSEYDPTRPFSEASMMGLLTNLADRELVHMINW
AKRVPGFVDLTLHDQVHLLECAWLEILMIGLVWRSMEHPGKLLFAPNLLLDRNQGKCVEG
MVEIFDMLLATSSRFRMMNLQGEEFVCLKSIILLNSGVYTFLSSTLKSLEEKDHIHRVLD
KITDTLIHLMAKAGLTLQQQHQRLAQLLLILSHIRHMSNKGMEHLYSMKCKNVVPLYDLL
LEMLDAHRLHAPTSRGGASVEETDQSHLATAGSTSSHSLQKYYITGEAEGFPATV (SEQ ID NO: 4)

FIG. 1

ETRYCAVCNDYASGYHYGVWSCEGCKAFFKRSIQGHNDYMCPATNQCTIDKNRRK
SCQACRLRKCYEVGMMKGGIRKDRRGG (SEQ ID NO: 5)

FIG. 2

MDPMIKRSKKNSLALSLTADQMVSALLDAEPPILYSEYDPTRPFSEASMMGLLTN
LADRELVHMINWAKRVPGFVDLTLHDQVHLLECAWLEILMIGLVWRSMEHPGKLL
FAPNLLLDRNQGKCVEGMVEIFDMLLATSSRFRMMNLQGEEFVCLKSIILLNSGV
YTFLSSTLKSLEEKDHIHRVLDKITDTLIHLMAKAGLTLQQQHQRLAQLLLILSH
IRHMSNKGMEHLYSMKCKNVVPLYDLLLEMLDAHRLHAP (SEQ ID NO: 6)

FIG. 3

```
ETRYCAVCNDYASGYHYGVWSCEGCKAFFKRSIQGHNDYMCPATNQCTIDKNRRKSCQAC
RLRKCYEVGMMKGGIRKDRRGGRMLKHKRQRDDGEGRGEVGSAGDMRAANLWPSPLMIKR
SKKNSLALSLTADQMVSALLDAEPPILYSEYDPTRPFSEASMMGLLTNLADRELVHMINW
AKRVPGFVDLTLHDQVHLLECAWLEILMIGLVWRSMEHPGKLLFAPNLLLDRNQGKCVEG
MVEIFDMLLATSSRFRMMNLQGEEFVCLKSIILLNSGVYTFLSSTLKSLEEKDHIHRVLD
KITDTLIHLMAKAGLTLQQQHQRLAQLLLILSHIRHMSNKGMEHLYSMCKNVVPLYDLL
LEMLDAHRLHAP
```

(SEQ ID NO: 7)

FIG. 4

```
ETRYCAVCNDYASGYHYGVWSCEGCKAFFKRSIQGHNDYMCPATNQCTIDKNRRKSCQAC
RLRKCYEVGMMKGGIRKDRRGGRMLKHKRQRDDGEGRGEVGSAGDMRAANLWPSPLMIKR
SKKNSLALSLTADQMVSALLDAEPPILYSEYDPTRPFSEASMMGLLTNLADRELVHMINW
AKRVPGFVDLTLHDQVHLLECAWLEILMIGLVWRSMEHPGKLLFAPNLLLDRNQGKCVEG
MVEIFDMLLATSSRFRMMNLQGEEFVCLKSIILLNSGVYTFLSSTLKSLEEKDHIHRVLD
KITDTLIHLMAKAGLTLQQQHQRLAQLLLILSHIRHMSNKGMEHLYSMCKNVVPLYDLL
LEMLDAHRLHAPTSRGGASVEETDQSHLATAGSTSSHSLQKYYITGEAEGFPATV
```

(SEQ ID NO: 8)

FIG. 5

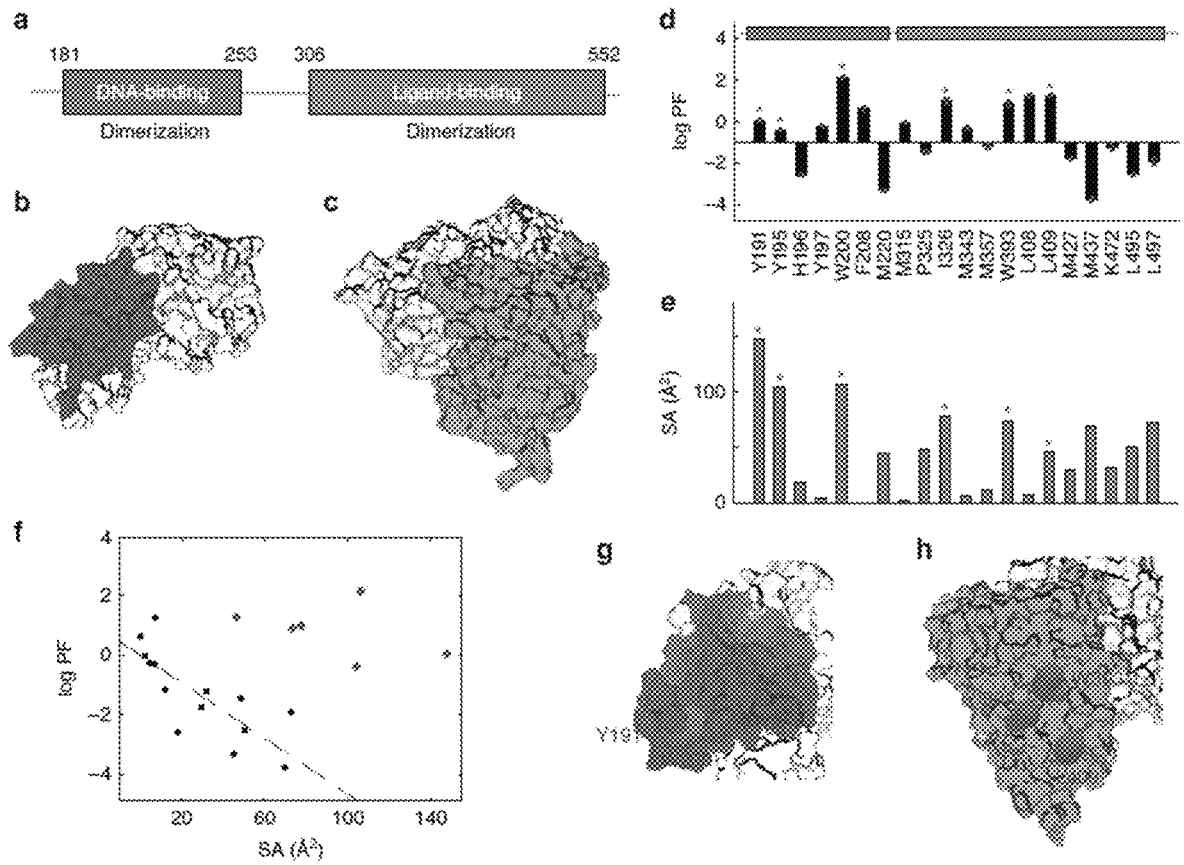

FIG. 6a-h

ETRYCAVCNDYASGYHYGVWSCEGCKAFFKRSIQGHNDYMCPATNQCTIDKNRRKSCQAC
RLRKCYEVGMMKGGIRKDRRGGRMLKHKRQRDDGEGRGEVGSAGDMRAANLWPSPLMIKR
SKKNSLALSLTADQMVSALLDAEPPILYSEYDPTRPFSEASMMGLLTNLADRELVHMINW
AKRVPGFVDLTLHDQVHLLECAWLEILMIGLVWRSMEHPGKLLFAPNLLLDRNQGKCVEG
MVEIFDMLLATSSRFRMMNLQGEEFVCLKSIILLNSGVYTFLSSTLKSLEEKDHIHRVLD
KITDTLIHLMAKAGLTLQQQHQRLAQLLLILSHIRHMSNKGMEHLYSMKCKNVVPLYDLL
LEMLDAHRLHAP (SEQ ID NO: 9)

FIG. 7

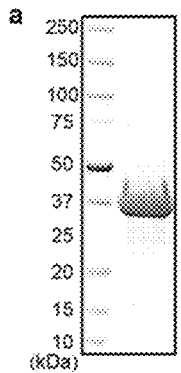

hERα<sup>CDE</sup> (E181-P552)
ETRYCAVCNDYASGYHYGVWSCEGCKAFFKRSIQGHNDYMCPATNQCTIDKNRRKSCQAC
RLRKCYEVGMMKGGIRKDRRGGRMLKHKRQRDDGEGRGEVGSAGDMRAANLWPSPLMIKR
SKKNSLALSLTADQMVSALLDAEPPILYSEYDPTRPFSEASMMGLLTNLADRELVHMINW
AKRVPGFVDLTLHDQVHLLECAWLEILMIGLVWRSMEHPGKLLFAPNLLLDRNQGKCVEG
MVEIFDMLLATSSRFRMMNLQGEEFVCLKSIILLNSGVYTFLSSTLKSLEEKDHIHRVLD
KITDTLIHLMAKAGLTLQQQHQRLAQLLLILSHIRHMSNKGMEHLYSMKCKNVVPLYDLL
LEMLDAHRLHAP (SEQ ID NO: 1)

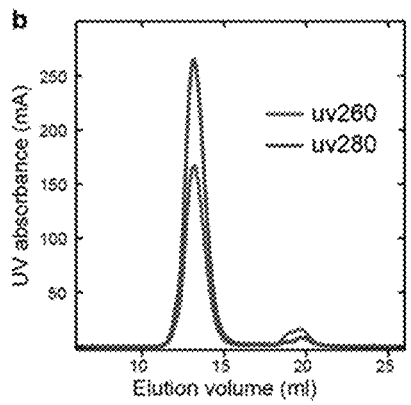
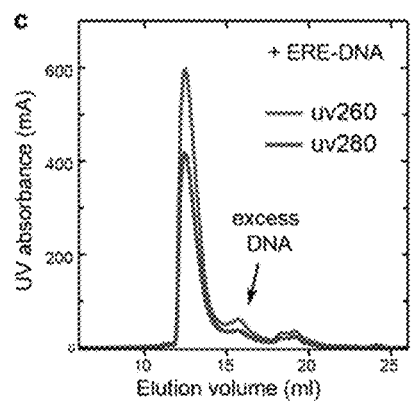
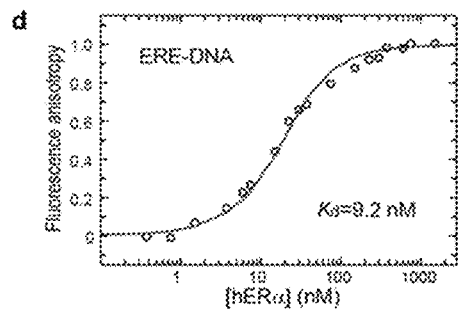
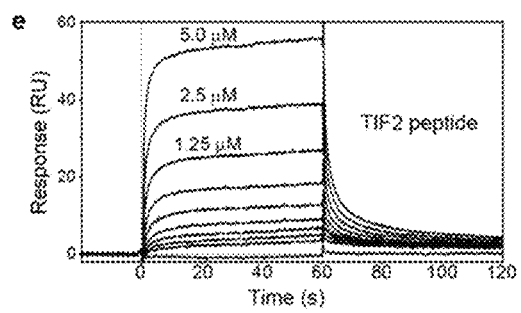

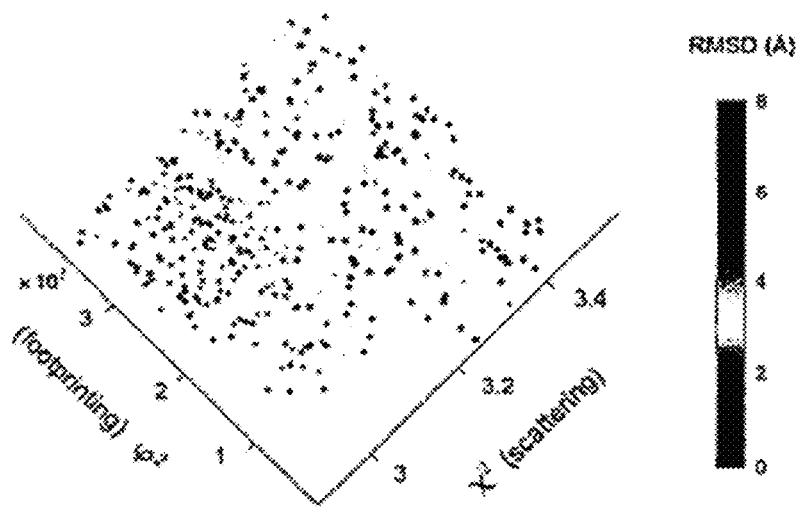
FIG. 13
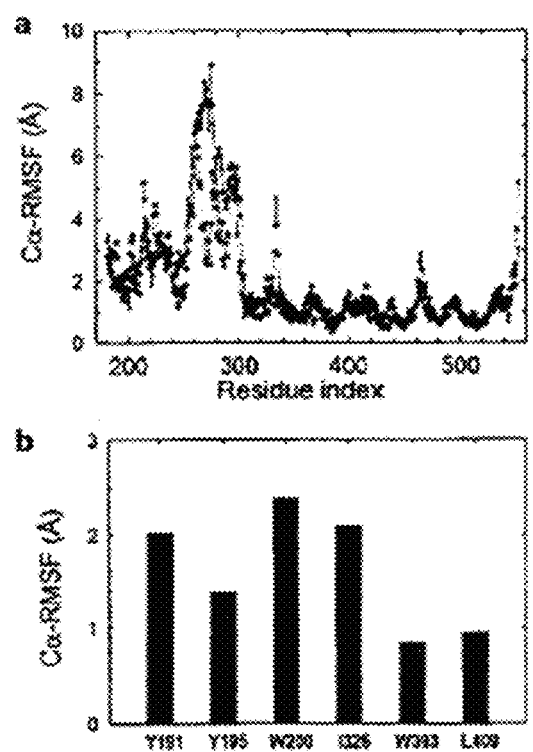
FIG. 14a-b

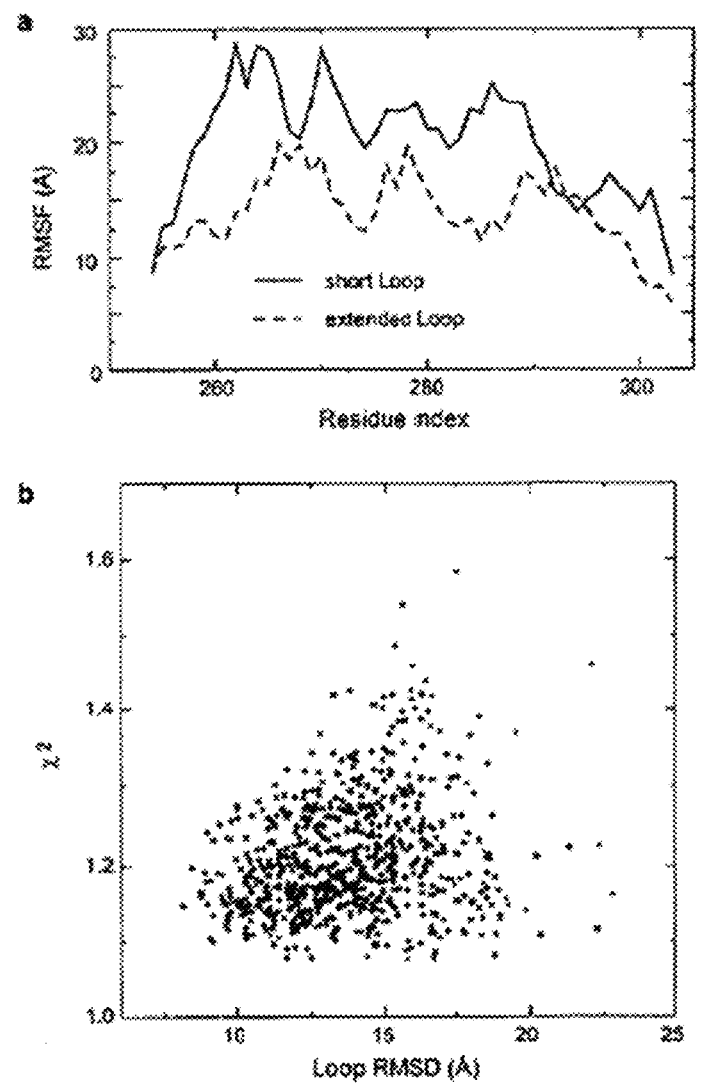
FIG. 15a-b

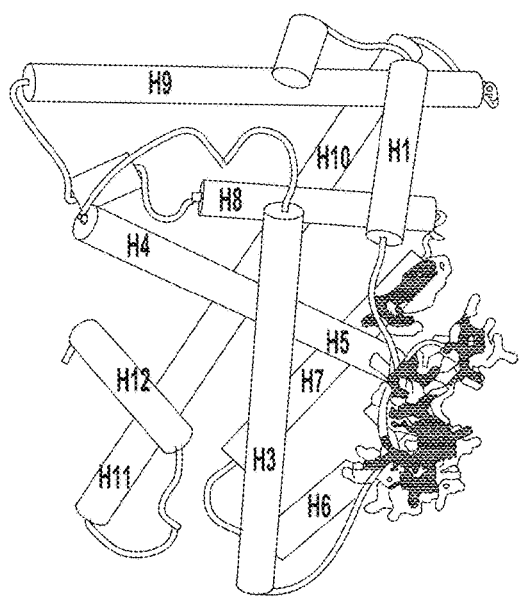
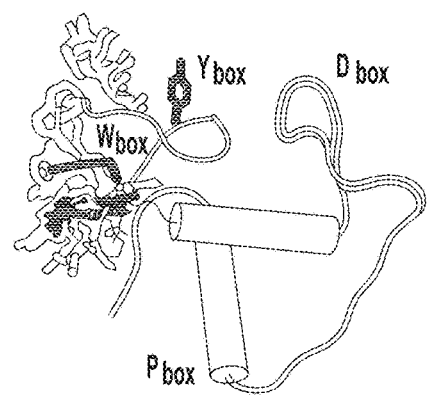
FIG. 16A    FIG. 16B
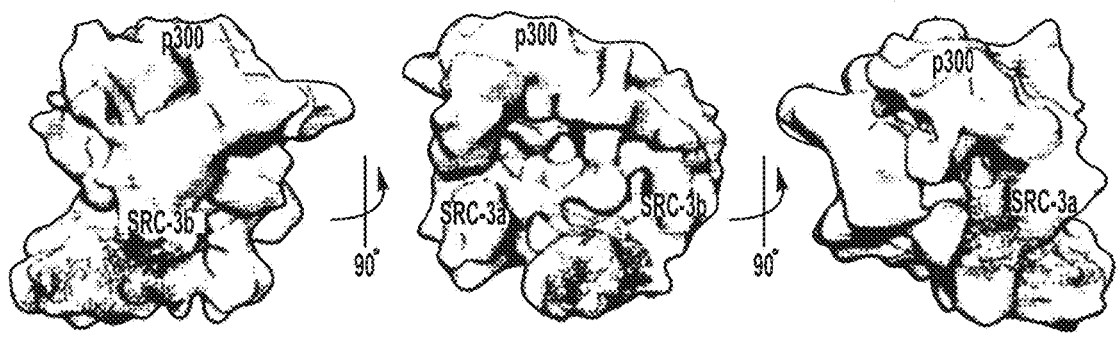
FIG. 17

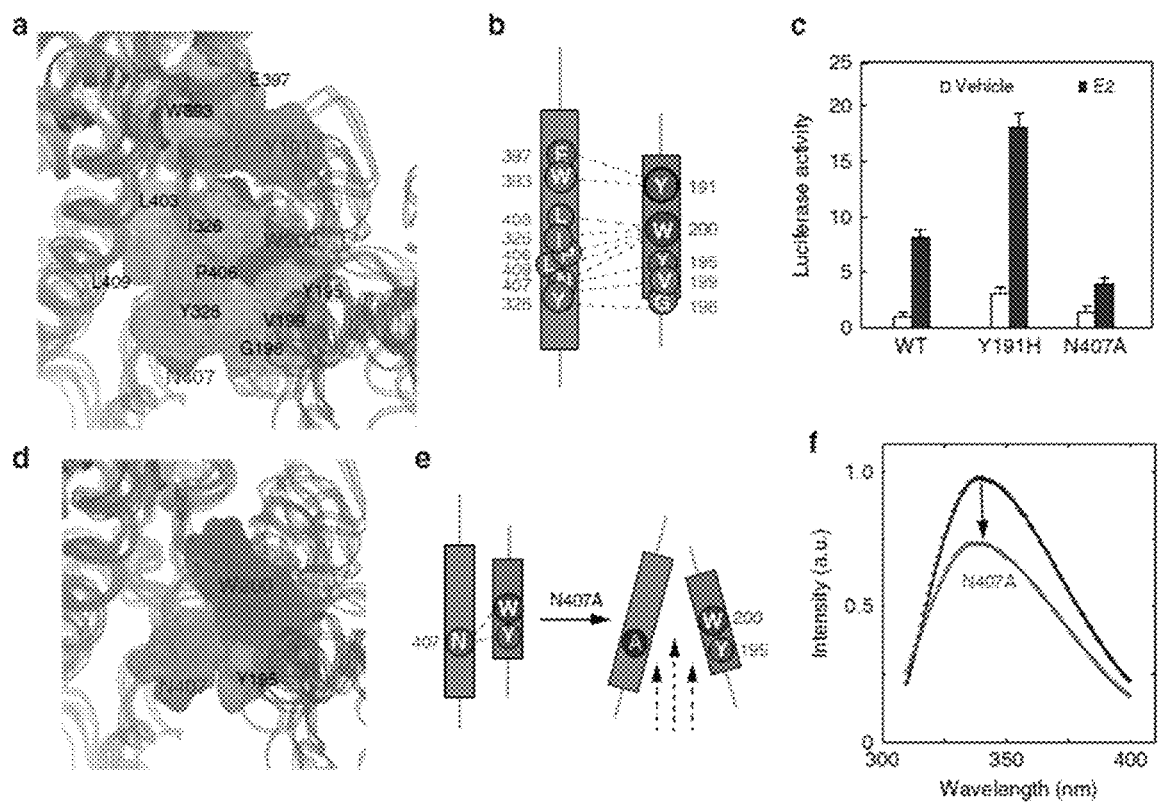
FIG. 18a-f

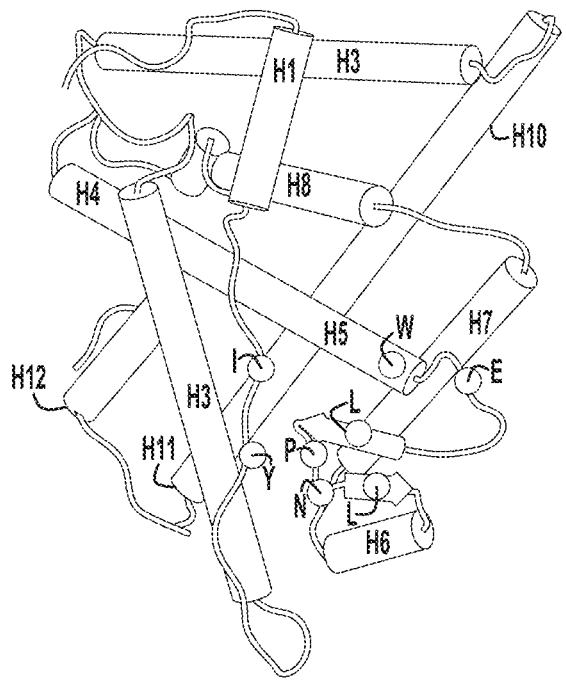
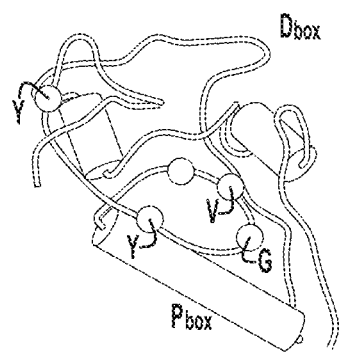
FIG. 19A
FIG. 19B
FIG. 20

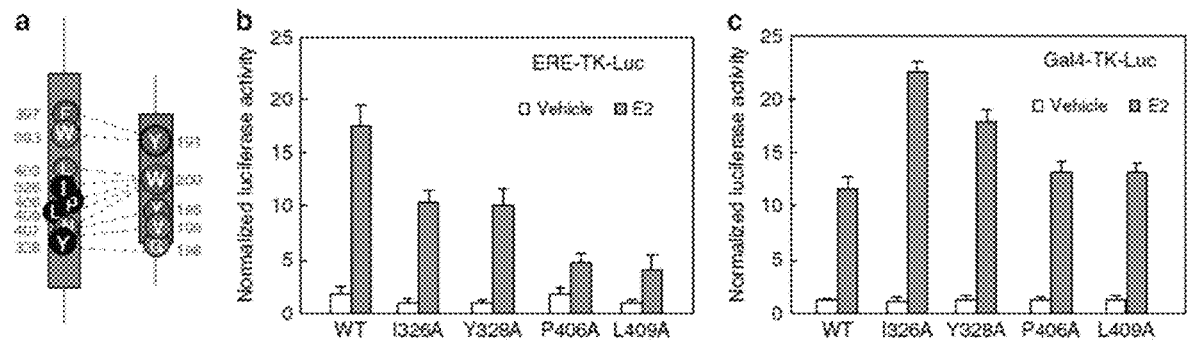
FIG. 21a-c
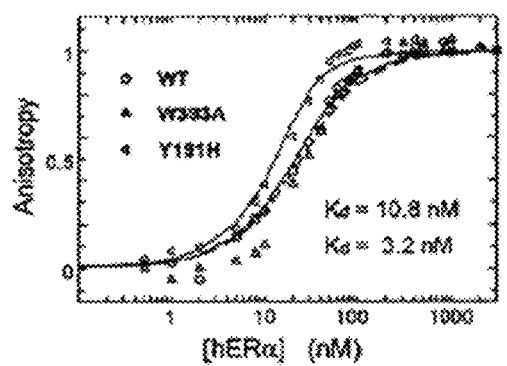
FIG. 22

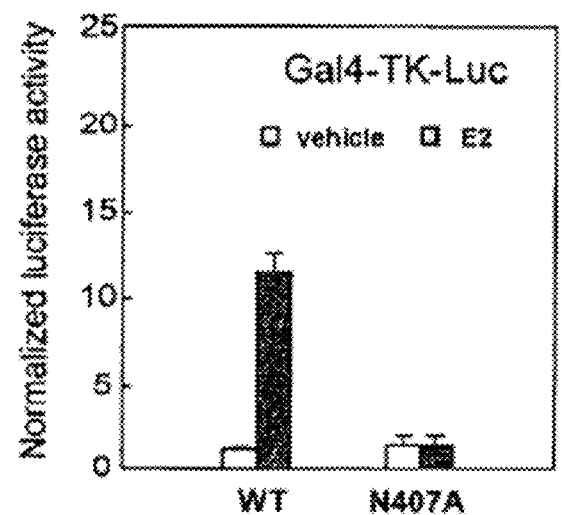
FIG. 23
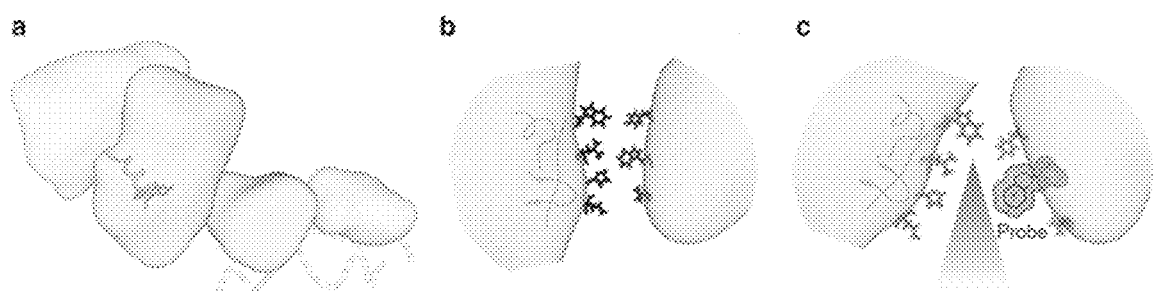
FIG. 24a-c

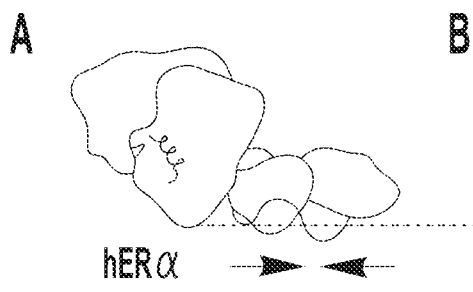
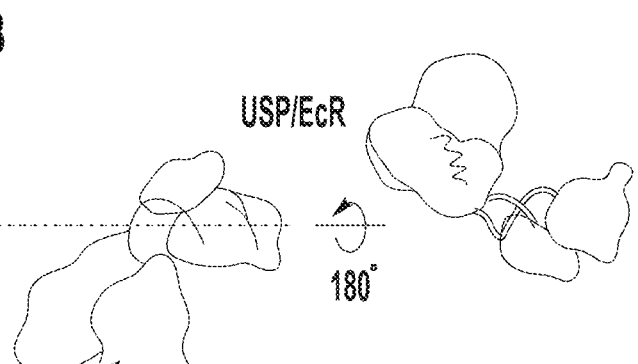
FIG. 25A  FIG. 25B
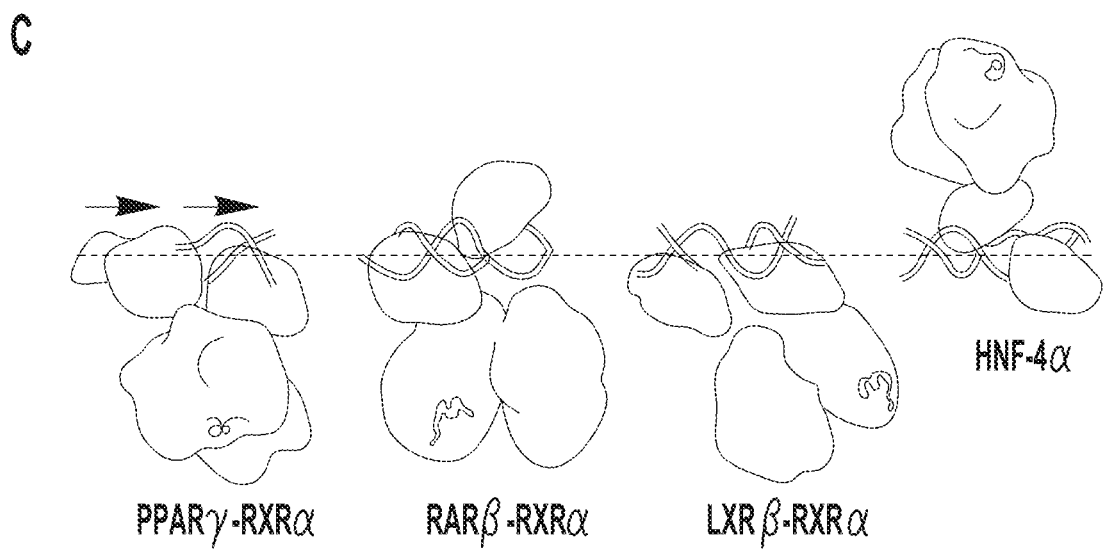
FIG. 25C
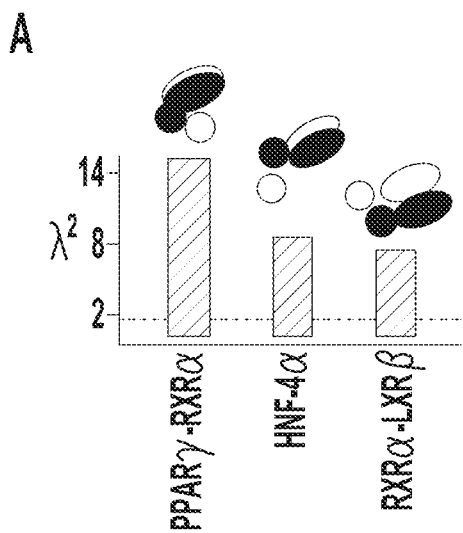
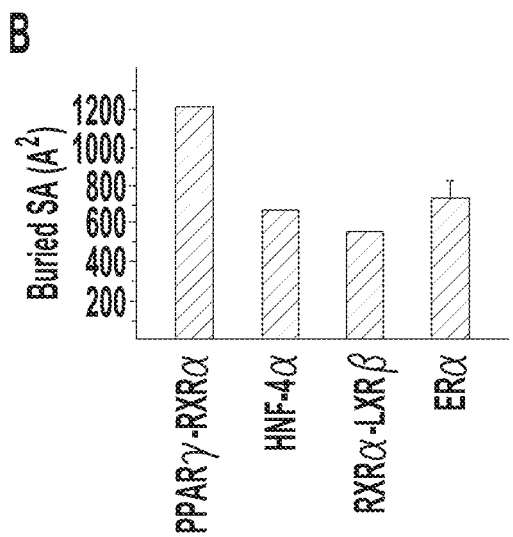
FIG. 26A  FIG. 26B

```
ETRYCAVCNDYASGYHYGVWSCEGCKAFFKRSIQGHNDYMCPATNQCTIDKNRRKSCQAC
RLRKCYEVGMMKGGIRKDRRGGRMLKHKRQRDDGEGRGEVGSAGDMRAANLWPSPLMIKR
SKKNSLALSLTADQMVSALLDAEPPILYSEYDPTRPFSEASMMGLLTNLADRELVHMINW
AKRVPGFVDLTLHDQVHLLECAWLEILMIGLVWRSMEHPGKLLFAPNLLLDRNQGKCVEG
MVEIFDMLLATSSRFRMMNLQGEEFVCLKSIILLNSGVYTFLSSTLKSLEEKDHIHRVLD
KITDTLIHLMAKAGLTLQQQHQRLAQLLLILSHIRHMSNKGMEHLYSMKCKNVVPLYDLL
LEMLDAHRLHAP
```

(SEQ ID NO: 13)

FIG. 27

MUTANT HUMAN ESTROGEN RECEPTOR-α AND METHODS OF USE THEREOF

RELATED APPLICATIONS

This application claims the benefit of U.S. Provisional Application Ser. No. 62/772,296, filed Nov. 28, 2018, entitled "A Genetically-Engineered Fluorescence Assay for Structure-Based Drug Discovery of Next-Generation Estrogen Receptor Inhibitors," and U.S. Provisional Application Ser. No. 62/893,856 filed Aug. 30, 2019, entitled "A Genetically-Engineered Fluorescence Assay for Structure-Based Drug Discovery of Next-Generation Estrogen Receptor Inhibitors." These provisional applications are hereby incorporated by reference in their entirety for all purposes.

GOVERNMENT FUNDING

This invention was made with government support under grant GM114056 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Nov. 22, 2019, is named CWR-028194_US_ORD_SL.txt and is 33,371 bytes in size.

TECHNICAL FIELD

The present disclosure relates generally to mutant proteins and their methods of use and, more particularly, to mutant estrogen receptors (ERs) and related methods for screening for potential therapeutic agents using the mutant ERs.

BACKGROUND

Estrogen receptor alpha (ERα) plays an important role in the development of various physiological functions; in particular, over 70% of breast cancers are ERα-positive. The gold standard treatment in ERα-positive breast cancer is oral tamoxifen, a selective estrogen receptor modulator (SERM). Over time or by chance mutation, ERα-positive breast cancer can become resistant to tamoxifen.

Human ERα (hERα) is a hormone-responsive nuclear receptor (NR) that consists of a DNA-binding domain (DBD) and a ligand-binding domain (LBD) that binds the physiological hormone, estrogen, and functions as a hormone-regulated transcription factor. Like other NRs, it contains a highly conserved DBD and a C-terminal 12-helical LBD. Several other NRs, including PPARγ-RXRα5, VDR-RXRα6, RARα-RXRα7, HNF-4α homodimer8, RXRα-LXRβ9, USP/EcP10, and more recently, RARβ-RXRα11, have been characterized with respect to their physical interactions and the allosteric communication between the DBD and LBD. These distinct DBD-LBD interactions mediate allosteric signal transduction in the function of the different NRs. However, for hERα, while the individual structures of the DBD and LBD domains are known, the overall architectural structure of the entire complex and the domain interactions have been unknown. This lack of information has made it difficult to dissect the inner-workings of receptor activation critical for hormonal signaling.

SUMMARY

The present disclosure relates generally to mutant proteins and their methods of use and, more particularly, to mutant ERs and related methods for screening for potential therapeutic agents using the mutant ERs.

In one aspect, the present disclosure can include an isolated mutant hERα comprising a DNA-binding domain (DBD), a ligand-binding domain (LBD), and an interface between the DBD and the LBD, wherein at least one tryptophan residue is mutated to a phenylalanine residue.

In another aspect, the present disclose can include a method for drug discovery comprising contacting a mutant hERα with a therapeutic agent to assess the effect of the therapeutic agent on the ability of hERα to regulate transcription, wherein the mutant hERα has a DBD, a LBD, and an interface between the DBD and the LBD, and wherein at least one tryptophan residue is mutated to a phenylalanine residue.

In another aspect, the disclosure can include a kit comprising a mutant human estrogen receptor alpha (hERα) comprising a DNA-binding domain (DBD), a ligand-binding domain (LBD), and an interface between the DBD and the LBD, wherein at least one tryptophan residue is mutated to a phenylalanine residue; at least one protein buffer; and instructions for using the kit to carry out a method of drug discovery.

BRIEF DESCRIPTION OF THE DRAWINGS

The foregoing and other features of the present disclosure will become apparent to those skilled in the art to which the present disclosure relates upon reading the following description with reference to the accompanying drawings, in which:

FIG. 1 provides the amino acid sequence for hERα (SEQ ID. NO: 4);

FIG. 2 provides the amino acid sequence for the DBD of hERα (SEQ ID. NO: 5);

FIG. 3 provides the amino acid sequence for the LBD of hERα (SEQ ID. NO: 6);

FIG. 4 provides the amino acid sequence for amino acids 181-552 of hERα (SEQ ID NO: 7);

FIG. 5 provides the amino acid sequence for amino acids 181-595 of hERα (SEQ ID NO: 8);

FIGS. 6(a)-(h) show the contact residues between the DBD and LBD identified by footprinting. FIG. 6(a) shows the structural domains of hERα. Human ERα contains a DBD, a LBD, and functions as a homodimer. FIG. 6(b) shows the crystal structure of the DBD dimer in complex with ERE-DNA. FIG. 6(c) shows the crystal structures of the LBD dimer in complex with estradiol and a coactivator TIF2 peptide. FIG. 6(d) is a graph showing the hydroxyl radical footprinting of hERα. High log PF values of six residues (*) indicate their involvement in domain contacts. Duplicates were performed and standard deviations are indicated. FIG. 6(e) is a graph showing the solvent accessibility surface area (SA) values of residue side chains calculated from the crystal structure of individual domains. FIG. 6(f) is a graph showing the correlation between log PF and SA values where differentiation of the six contact residues (4) is shown from the rest of 14 residues (dots). The latter have a Pearson's correlation coefficient −0.77 (p-value 0.001). FIGS. 6(g) and (h) are diagrams showing the structural mapping of contact residues where the contact residues are Y191/Y195/W200 on the surface of the DBD and I326/W393/L409 on the LBD.

FIG. 7 provides the amino acid sequence for amino acids E181-P552 of hERα (SEQ ID NO: 9);

FIGS. 8(a)-(e) are graphs relating to the purification and characterization of recombinant hERα. FIG. 8(a) shows the expression of hERα$^{CDE}$ specifically the SDS-PAGE gel of recombinant hERα$^{CDE}$ (E181-P552) (SEQ ID NO: 1). FIGS. 8(b) and (c) show the purification of hERα$^{CDE}$, specifically size exclusion chromatography of hERα$^{CDE}$ in the absence (b) or presence (c) of ERE-DNA. Shown are the absorbance at 260 nm and 280 nm of hERα$^{CDE}$ in the presence of estradiol and a coactivator TIF2 peptide. FIG. 8(d) shows the binding to ERE-DNA of hERα$^{CDE}$. Fluorescence anisotropy was measured using a fluorescent dye, 6-Carboxyfluorescein (6-FAM) to label the 5' end of ERE-DNA, yielding an apparent binding affinity of $K_d$=9.2 nM. Data of 2.8-µM hERα$^{CDE}$ in the presence of E2 were used as a saturation level and free 20-nM DNA data as a baseline. FIG. 8(e) shows the binding of a coactivator TIF2 peptide to hERα$^{CDE}$. The binding of the hERα to a coactivator TIF2 peptide (sequence KENALLRYLLDKDD) (SEQ ID NO: 2) in the presence of E2 and ERE-DNA was measured by surface plasmon resonance (SPR). Hereinafter, hERα$^{CDE}$ in the estradiol E2, ERE-DNA, and a coactivator TIF2 peptide is referred to as hERα$^{complex}$.

FIG. 12(a) shows the fit of computationally generated conformations (dot) simultaneously assessed against hydroxyl radical protein footprinting ($φ^2$) and small-angle X-ray scattering ($χ^2$). Lower $χ^2$ and $φ^2$ values are better in fitting. The best-fit ensemble structures lie at the bottom corner of the fit plot, below the dashed line. FIG. 12(b) shows an ensemble of best-fit hERα structures. It contains both LBD monomers and DBD monomers. The structure models are within 3 Å Cα-RMSD of the best-fit structure. FIG. 12(c) shows a rotated view of the best-fit hERα structures. FIG. 12(d) shows the goodness of fit to measured SAXS data. Theoretical SAXS data were the ensemble average of the set of hERα structures above. The scattering intensity, $log_{10}I(q)$, is plotted as a function of the scattering angle (q). The goodness of fit $χ^2$=1.2. Inserted is the Guinier plot with a linear fit, yielding the radius of gyration $R_g$=38.0±0.3 Å. The bottom graph shows residuals from subtraction between calculated and experimental profiles. A total of six scattering images were used and standard deviations were indicated. FIG. 12(e) shows the goodness of fit to footprinting data. Measured footprinting protection factors (log PF) are plotted against average accessible surface areas (SA) derived from the ensemble structures. Linear correlation coefficient is p=−0.95. A total of seven structures were used for ensemble calculations and standard deviations were indicated.

FIG. 13 is a graph showing Ca-RMSD of docking structure models from the best-fit structure. Both LBD and DBD were included, except the domain-connecting hinge.

FIGS. 14(a)-(b) are graphs showing Cα-RMS fluctuations (RMSF) from the hERα structure-ensemble. Residue RMSF values of both chains of the hERα homodimer (FIG. 14(a)) and for those footprinting detected interfacial residues (FIG. 14(b)).

FIGS. 15(a)-(b) are graphs showing loop flexibility and its contribution to scattering fitting. FIG. 15(a) shows Cα-atom RMS fluctuation (Cα-RMSF) of the DBD-LBD connecting loops (residues 254-303) for each peptide chain (short and extended). FIG. 15(b) shows the goodness of fit $χ^2$ as a function of the loop's RMSD using its average structure as a reference. Scattering was calculated using the program Crysol. The loop structures were generated using the program loopy (http://honig.c2b2.columbia.edu/loopy/), where a set of 100 structures was used for each of hERα ensemble-structures (eight as shown in FIG. 12(e)), yielding the value of $X^2$=1.2±0.1.

FIGS. 16(a)-(b) show the overlap of interfacial residues from individual domains and from the hERα ensemble-structures. Contact residues are colored on the LBD surface FIG. 16(a) and the DBD surface FIG. 16(b).

FIG. 17 shows the fitting of hERα ensemble structures into a 22-Å EM map. The ensemble-structures of hERα$^{complex}$ were rigidly docked into the EM map (EMD-8832) of the full-length hERα in complex with coactivators (SRC-3a/SRC-3b/p300). The coactivator peptide (KE-NALLRYLLDKDD) (SEQ ID NO: 3) used in the instant sample was consistent with the positions of coactivators SRC-3a and SRC-3b as shown in the EM map.

FIGS. 18(a)-(f) show the DBD-LBD interface and its functional relevance. FIG. 18(a) shows a close-up view of the DBD-LBD interface. FIG. 18(b) shows a cartoon of interfacial residues. Dashed lines indicate a probability >75% of making a residue contact within the structure ensemble. FIG. 18(c) shows the effect of interfacial mutations on ER transcription activity. The Y191H mutation increases the transcription luciferase activity of the receptor, while N407 Å reduces the activity. Triplicates were carried out and standard deviations were indicated. FIG. 18(d) shows the tryptophan fluorescence site at W200. Shown are interactions between hydrophobic residues N407, Y195, and W200 at the interface. FIG. 18(e) is a schematic representation of tryptophan surroundings upon mutation. Illustrated are possible structural changes near W200 before and after mutation. FIG. 18(f) is a graph showing quenching of tryptophan fluorescence. Emission fluorescence intensity is reduced in mutant N407A. A protein concentration of 0.1 mg/ml was used before and after mutation. Excitation was at 295 nm.

FIGS. 19(a)-(b) show schematic drawings of hERα residues involved in the LBD-DBD interface. FIG. 19(a) is a drawing showing that the LBD consists of 12 helices and two β-strands (s1 and s2 between helices H5 and H6). The interfacial residues are I326, Y328, W393, E397, L403, P406, N407, and L409. They form a shallow and nearly flat surface, which is distant from helix H12 (covering the ligand binding pocket) and coactivator binding sites (near helices H3 and H4). FIG. 19(b) is a drawing showing that the contact residues from the DBD side are Y191, Y195, G198, V199, and W200, before the first helix of the DBD.

FIG. 20 is a diagram showing the LBD surface involved in DBD-LBD interactions. A modest-sized pocket (black) consists of nine residues, I326, Y328, W393, E397, L403, P406, N407, and L409 on the molecular surface of the LBD (ribbons).

FIGS. 21(a)-(c) show the transcriptional regulation of mutations at interfacial LBD residues. FIG. 21(a) shows the sites of LBD mutation (I326, Y328, P406, and L409), highlighted in black circles. FIGS. 21(b) and (c) show the transient transfection reporter activity of the hERα and the Gal4-DBD/hERα-LBD fusion protein, using an ERE-TK-Luc (b) or a Gal4-TK-Luc reporter construct (c), respectively. Triplicates were carried out and standard deviations are indicated FIG. 22 is a graph showing that mutation of Y191H increases DNA-binding. Y191H increases the receptor's DNA-binding affinity to $K_d$=3.2 nM, compared to the WT binding affinity $K_d$=9.2 nM. As a control, the W393A mutation has little change in its DNA-binding affinity $K_d$=10.8 nM.

FIG. 23 is a graph showing the transient transfection reporter activity of the wild-type hERα and the mutant N407 Å from the Gal4-DBD/hERα-LBD fusion protein using a Gal4-TK-Luc reporter construct when treated with estradiol (E2).

FIGS. 24(a)-(c) are diagrams showing the multidomain architecture and cross-talk at the domain interface of the hERα. FIG. 24(a) shows that the hERα homodimeric complex contains both LBDs and DBDs. A hormone ligand is capped underneath the LBD's C-terminal helix H12 (ribbon). FIG. 24(b) shows that the LBD-DBD interface consists of the LBD's two β-strands, distant from the ligand-binding pocket and coactivator-binding sites. Disruption of this interfacial cross-talk, which serves as an allosteric channel to transmit the signaling of ligand binding from the LBD to a distant DBD, suppresses hormone-induced transcription. FIG. 24(c) shows the alteration of the domain cross-talk at the structural level is monitored by intrinsic tryptophan fluorescence (i.e., W200 in the middle of the interface as a probe), using the genetically engineered hERα construct.

FIGS. 25(a)-(c) are diagrams showing the schematic representation of multidomain architectures of nuclear receptor complexes in complex with DNA of inverted repeat (IR) and direct repeat (DR). FIG. 25(a) shows the hERα in complex with IR ERE-DNA (SASBDB entry SASDDU8; https://www.sasbdb.org/data/SASDDU8). FIG. 25(b) shows the IR-bound USP/EcR (PDB entry 4UMM). A rotated view is shown for comparison with hERα. FIG. 25(c) shows the DR-bound complexes of PPARγ-RXRα (PDB entry 3DZY), RARβ-RXRα (PDB entry 5UAN), RXRα-LXRβ (PDB entry 4NQA), and HNF-4α (PDB entry 4IQR). All structures are shown by aligning the DNA (the 5'-half of the first strand).

FIGS. 26(a)-(b) are graphs showing the structural difference among multi-domain NRs. FIG. 26(a) shows the large difference in overall architecture. Mismatch of domain-domain organizations of other NRs is demonstrated by their large differences with experimental SAXS data of hERα$^{complex}$. A structural model of hERα$^{CDE}$ was built by threading of hERα$^{CDE}$ sequence onto each NR structure to calculate its theoretical scattering profile. The resulting $\chi^2$ values are 14.6, 8.0, and 6.9 for PPARγ-RXR, HNF-4α and LXRβ-RXRα, respectively. The domain-connecting hinge was built using the loop modeling package loopy (http://honig.c2b2.columbia.edu/loopy). FIG. 26(b) shows the buried LBD surface. Buried solvent accessible surface areas (SA; s.d. from the structure-ensemble) are the difference of the LBD in the absence and presence of DBD. SA was calculated with a probe size of 1.4 Å using the software VMD;

FIG. 27 provides the amino acid sequence for amino acids 181-552 of hERα (SEQ ID NO: 13).

DETAILED DESCRIPTION

I. Definitions

Figure 9:
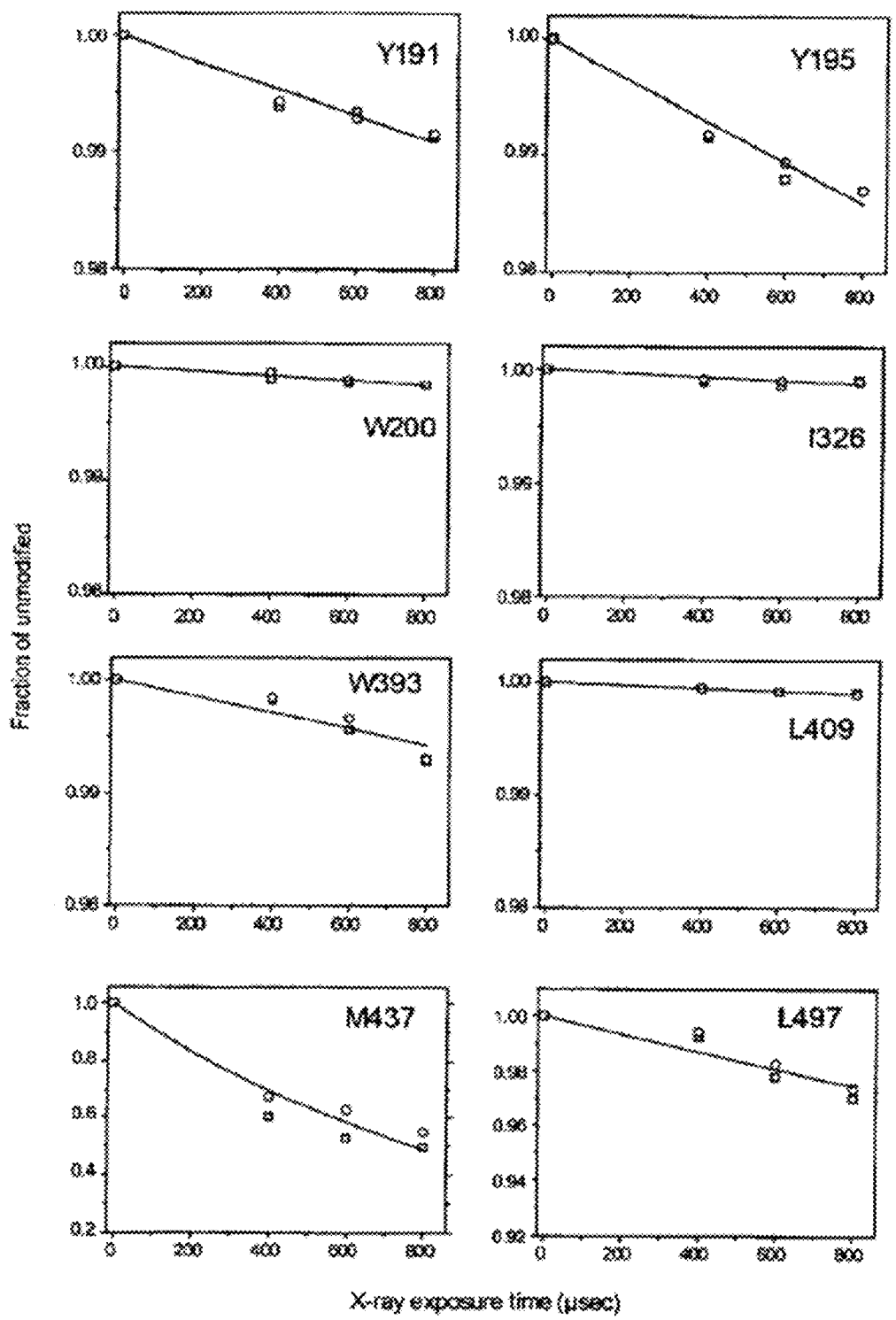
FIG. 9 shows dose-response plots of footprinting as a function of X-ray exposure time. The lines correspond to the least-squares fit of the averages of duplicate dose-dependent data (i.e., a normalized fraction of unmodified residues), each yielding a rate of footprinting.

Unless otherwise defined, all technical terms used herein have the same meaning as commonly understood by one of ordinary skill in the art to which the present disclosure pertains.

In the context of the present disclosure, the singular forms "a," "an" and "the" can also include the plural forms, unless the context clearly indicates otherwise.

The terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the terms "cancer" and "tumor" are synonymous terms. The term "cancer" or "tumor" can refer to the presence of cells possessing characteristics typical of cancer-causing cells, such as uncontrolled proliferation, immortality, metastatic potential, rapid growth and proliferation rate, and certain characteristic morphological features. Cancer cells are often in the form of a tumor, but such cells can exist alone within an animal, or can be a non-tumorigenic cancer cell.

As used herein, the term "hERα" can refer to human estrogen receptor alpha, which comprises amino acids 1-595 (SEQ ID NO: 4) (FIG. 1).

As used herein, the term "mutant hERα" can refer to any non-native hERα, hERα peptide, or fragment thereof.

As used herein, the term "genetically engineered" can refer to the artificial manipulation, modification, and/or recombination of DNA or other nucleic acid molecules in order to modify a cell, a population of cells, organism, or population of organisms.

As used herein, the term "DNA-binding domain" or "DBD" can refer to the DBD of hERα or mutant hERα. The DBD can comprise amino acids 181-262 of hERα (SEQ ID NO: 5) (FIG. 2) or mutant hERα. The DBD is an independently-folded protein domain that contains at least one structural motif that recognizes, binds to, or associates with double- or single-stranded DNA.

As used herein, the term "ligand binding domain" or "LBD" can refer to the LBD of hERα or mutant hERα. The LBD can comprise amino acids 297-552 of hERα (SEQ ID NO: 6) (FIG. 3) or mutant hERα. The LBD is the domain responsible for hormone binding.

As used herein, the term "therapeutic agent" can refer to, e.g., small molecule compounds (e.g., small molecule drugs), nucleic acids (e.g., siRNA, aptamers, short hairpin RNAs, antisense oligonucleotides, ribozymes, antagomirs, microRNA mimics or DNA) or polypeptides, e.g., antibodies (e.g., full length antibodies or antigen-binding fragments thereof, Fab fragments, or scFv fragments).

As used herein, the term "transcription" can refer to a process in which a particular segment of DNA is copied into RNA by RNA polymerase.

As used herein, the term "fluorescence" can refer to the process whereby a molecule absorbs light of a specific wavelength and emits light at a different wavelength. As used herein, the term "tryptophan fluorescence" refers to the fluorescence emission of tryptophan residue(s) in a particular protein, such as hERα or a mutant hERα. Tryptophan fluorescence can be measured by excitation of a protein at about 280 nm, and then observing the fluorescence emission spectra of the protein at 300-400 nm. By "about 280 nm" it is meant that excitation could occur at wavelengths from 250-310 nm, but with the peak generally around 295 nm. One skilled in the art would understand that the actual emission wavelength can vary depending upon the polarity of the environment containing the tryptophan.

As used herein, the term "substantially identical," can refer to an identity or homology of at least 70%, at least 75%, at least 80%, at least 85%, at least 90%, 91%, 92%, 93%, 94%, 95%, 96%, 97%, 98%, 99%, or more.

As used herein, the terms "homology" or "identity," can refer to sequence similarity between two polypeptide sequences, with identity being a more strict comparison. The phrases "percent identity or homology" and "% identity or homology" refer to the percentage of sequence similarity found in a comparison of two or more polypeptide sequences. Identity can be determined by comparing a position in each sequence that can be aligned for purposes of comparison. When a position in the compared sequence is occupied by the same amino acid, then the molecules are identical at that position. A degree of identity of polypeptide sequences is a function of the number of identical amino acids at positions shared by the polypeptide sequences. A degree of homology or similarity of polypeptide sequences is a function of the number of amino acids at positions shared by the polypeptide sequences.

To determine the percent identity of two amino acid sequences, the sequences are aligned for optimal comparison purposes (e.g., gaps can be introduced in the sequence of a first amino acid sequence for optimal alignment with a second amino sequence). The amino acid residues at corresponding amino acid positions are then compared. When a position in the first sequence is occupied by the same amino acid residue as the corresponding position in the second sequence, then the molecules are identical at that position. The percent identity between the two sequences is a function of the number of identical positions shared by the sequences (i.e., identity=# of identical positions/total # of positions (e.g., overlapping positions)×100). The determination of percent identity between two sequences can be accomplished using a mathematical algorithm.

As used herein, the terms "isolated" or "purified" can refer to proteins that are substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, less than about 20%, less than about 10%, or less than about 5% (by dry weight) of heterologous protein (also referred to herein as a "contaminating protein"). When the protein is recombinantly produced, it can be substantially free of culture medium, i.e., culture medium represents less than about 20%, less than about 10%, or less than about 5% of the volume of the protein preparation. When the protein is produced by chemical synthesis, it can be substantially free of chemical precursors or other chemicals, i.e., it is separated from chemical precursors or other chemicals which are involved in the synthesis of the protein. Accordingly, such preparations of the protein have less than about 30%, less than about 20%, less than about 10%, less than about 5% (by dry weight) of chemical precursors or compounds other than the polypeptide of interest.

Also herein, where a range of numerical values is provided, it is understood that each intervening value is encompassed within the present disclosure. The upper and lower limits of these smaller ranges may independently be included in the smaller ranges, and are also encompassed within the present disclosure, subject to any specifically excluded limit in the stated range. Where the stated range includes one or both of the limits, ranges excluding either or both of those included limits are also included in the present disclosure.

II. Overview

The present disclosure relates generally to mutant proteins and their methods of use and, more particularly, to mutant estrogen receptors (ERs) and related methods for screening for potential therapeutic agents using the mutant ERs.

The present disclosure is based, at least in part, on the full structural elucidation of hERα and the characterization of its DBD-LBD interactions. It has been discovered that hERα is a hormone-responsive nuclear receptor that contains both a DBD and a LBD that exhibits an asymmetric organization that resembles an asymmetric L-shaped "boot". The DBD-LBD interface is mainly composed of hydrophobic contacts between the DBD's residues, including Y191, Y195, G198, V199, and W200 right before the first helix of the DBD and the LBD's eight contact residues, including I326, Y328, W393, E397, L403, P406, N407, and L409. The LBD contact residues are positioned in the two-strand region between helices H5 and H6 (L403/P406/N407/L409), the end of helix H5 (W393), and the loop region between helices H1 and H3 (I326/Y328). The distinctive assembly of the hERα DBD and LBD reveals a previously uncharacterized domain interface that regulates hERα's allosteric function through a signaling mechanism mediated by inter-domain crosstalk. Advantageously, this newly characterized domain interface provides a new target for drug discovery by, for example, providing a genetically engineered mutant hERα that can be used to screen for therapeutic agents that target and bind to this newly discovered interface.

III. Mutant hERα

One aspect of the present disclosure can include a genetically-engineered mutant hERα (herein referred to as a "mutant hERα") comprising a DBD, a LBD, and an interface between the DBD and the LBD, wherein at least one tryptophan residue is mutated to a phenylalanine residue. Tryptophan residues that can be mutated to a phenylalanine residue include W292, W360, W383 and W393. It will be appreciated that any one or any combination of these tryptophan residues can be mutated to a phenylalanine residue (or residues) as part of the mutant hERα of the present disclosure. The tryptophan residue, W200, is not mutated (i.e., it is kept native) so that it can act as an intrinsic fluorescence probe.

In some instances, the mutant hERα can comprise a polypeptide having the amino acid sequence of SEQ ID NO: 4 except that at least one tryptophan residue is mutated to a phenylalanine residue. In some instances, the mutant hERα can comprise a polypeptide having the amino acid sequence of SEQ ID NO: 4 except that at least two, at least three, or at least four of the tryptophan residues are mutated to phenylalanine residues. In one example, the mutant hERα can comprise a polypeptide having the amino acid sequence of SEQ ID NO: 4 except that only one tryptophan residue (e.g., W393) is mutated to a phenylalanine residue. In another example, the mutant hERα can comprise a polypeptide having the amino acid sequence of SEQ ID NO: 4 except that only two, only three, or only four tryptophan residues are mutated to phenylalanine residues. In another example, the mutant hERα can comprise a polypeptide having the amino acid sequence of SEQ ID NO: 4 except that at least one tryptophan residue, other than W200, is mutated to a phenylalanine residue; that is, tryptophan residue W200 is not mutated. In such instances, it is advantageous that W200 remains unmodified (non-mutated) so that it can act as an intrinsic fluorescence probe.

Alternatively, in some instances, the mutant hERα can comprise a polypeptide having a substantially identical amino acid sequence to SEQ ID NO: 4, except that at least one tryptophan residue is mutated to a phenylalanine residue. For example, the mutant hERα can comprise a polypeptide having a substantially identical amino acid sequence as SEQ ID NO: 4 except that at least two, at least three, or at least four of the tryptophan residues are mutated to phenylalanine residues. In another example, the mutant hERα can comprise a polypeptide having a substantially identical amino acid sequence as SEQ ID NO: 4 except that only one tryptophan residue (e.g., W393) is mutated to a phenylalanine residue. In yet another example, the mutant hERα can comprise a polypeptide having a substantially identical amino acid sequence as SEQ ID NO: 4 except that only two, only three, or only four tryptophan residues are mutated to phenylalanine residues. In a further example, the mutant hERα can comprise a polypeptide having a substantially identical amino acid sequence as SEQ ID NO: 4 except that at least one tryptophan residue, other than W200, is mutated to a phenylalanine residue; that is, tryptophan residue W200 is not mutated. In such instances, it is advantageous that W200 remains unmodified (non-mutated) so that it can act as an intrinsic fluorescence probe.

In other instances, the mutant hERα can comprise a fragment or portion of a polypeptide including the amino acid sequence of SEQ ID NO: 4 except that at least one tryptophan residue is mutated to a phenylalanine residue. In one example, the mutant hERα can comprise amino acid residues 181-552 of SEQ ID NO: 4 (SEQ ID NO: 7) (FIG. 4), except that at least one tryptophan residue is mutated to a phenylalanine residue. In another example, the mutant hERα can comprise the amino acid residues 181-595 of SEQ ID NO: 4 (SEQ ID NO: 8) (FIG. 5), except that at least one tryptophan residue is mutated to a phenylalanine residue. In some instances, the mutant hERα comprises a fragment or portion of a polypeptide having the amino acid sequence of SEQ ID NO: 4 except that at least two, at least three, or at least four of the tryptophan residues are mutated to phenylalanine residues. In one example, the mutant hERα can comprise a fragment or portion of a polypeptide having the amino acid sequence of SEQ ID NO: 4 except that only one tryptophan residue (e.g., W393) is mutated to a phenylalanine residue. In another example, the mutant hERα can comprise a fragment or portion of a polypeptide having the amino acid sequence of SEQ ID NO: 4 except that only two, only three, or only four tryptophan residues are mutated to phenylalanine residues. In another example, the mutant hERα can comprise a fragment or portion of a polypeptide having the amino acid sequence of SEQ ID NO: 4 except that at least one tryptophan residue at the interface between the DBD and the LBD, other than W200, is mutated to a phenylalanine residue; that is, tryptophan residue W200 is not mutated. In such instances, it is advantageous that W200 remains unmodified (non-mutated) so that it can act as an intrinsic fluorescence probe.

Alternatively, in some instances, the mutant hERα can comprise a fragment or portion of a polypeptide having a substantially identical amino acid sequence as SEQ ID NO: 4 except that at least one tryptophan residue is mutated to a phenylalanine residue. In one example, the mutant hERα can comprise an amino acid sequence substantially identical to residues 181-552 of SEQ ID NO: 4, except that at least one tryptophan residue is mutated to a phenylalanine residue. In another example, the mutant hERα can comprise an amino acid sequence that is substantially identical to residues 181-594 of SEQ ID NO: 4, except that at least one tryptophan residue is mutated to a phenylalanine residue. In some instances, the mutant hERα comprises a fragment or portion of a polypeptide having a substantially identical amino acid sequence as SEQ ID NO: 4 except that at least two, at least three, or at least four of the tryptophan residues are mutated to phenylalanine residues. In one example, the mutant hERα can comprise a fragment or portion of a polypeptide having a substantially identical amino acid sequence as SEQ ID NO: 4 except that only one tryptophan residue (e.g., W393) is mutated to a phenylalanine residue. In another example, the mutant hERα can comprise a fragment or portion of a polypeptide having a substantially identical amino acid sequence as SEQ ID NO: 4 except that only two, only three, or only four tryptophan residues are mutated to phenylalanine residues. In another example, the mutant hERα can comprise a fragment or portion of a polypeptide having a substantially identical amino acid sequence as SEQ ID NO: 4 except that at least one tryptophan residue, other than W200, is mutated to a phenylalanine residue; that is, tryptophan residue W200 is not mutated. In such instances, it is advantageous that W200 remains unmodified (non-mutated) so that it can act as an intrinsic fluorescence probe.

Another aspect of the present disclosure can include a method for preparing a mutant hERα. In one instance, a native hERα protein can be isolated from cells or a tissue source using standard isolation and protein purification techniques. Following isolation of the native mutant hERα protein, one or more of the tryptophan residues can be selectively mutated into phenylalanine residues by methods known in the art. Other methods for creating mutant polypeptides and proteins are known in the art.

IV. Methods

Another aspect of the present disclosure is directed to methods for drug discovery, such as the discovery of hERα inhibitors.

In one instance, the method is directed to the identification of a therapeutic agent capable of inhibiting hERα's ability to regulate transcription. The term "inhibiting" can mean that hERα's ability to regulate transcription is decreased in the presence of the therapeutic agent when compared to the absence of the therapeutic agent. The method can include contacting a mutant hERα with a therapeutic agent to assess, for example, the effect of the therapeutic agent on the ability of hERα to regulate transcription, wherein the mutant hERα has a DBD, a LBD, and an interface between the DBD and the LBD, and wherein at least one tryptophan residue is mutated to a phenylalanine residue. In one aspect, the effect that the therapeutic agent has on the ability of hERα to regulate transcription can be determined by first carrying out a tryptophan fluorescence assay as described below. If a change in tryptophan fluorescence is detected, a transcription assay can be carried out to measure the inhibitive properties of the therapeutic agent.

A further aspect of the present disclose is directed to a method for detecting disruption to the hERα DBD-LBD interface by a therapeutic agent, where the method includes contacting a mutant hERα with a therapeutic agent, wherein the mutant hERα has a DBD, a LBD, and an interface between the DBD and the LBD, and wherein at least one tryptophan residue is mutated to a phenylalanine residue, and monitoring the change in tryptophan fluorescence of the mutant hERα. The tryptophan fluorescence of the mutant hERα can be monitored using a fluorescence assay protocol as described below. In some instances, a decrease in tryptophan fluorescence as compared to a control indicates that the therapeutic agent binds to the mutant hERα. In other instances, an increase in tryptophan fluorescence as compared to a control indicates that the therapeutic agent binds to the mutant hERα.

Another aspect of the present disclosure is directed to a method for screening for estrogen receptor inhibitors where the method includes contacting a mutant hERα with an inhibitor drug candidate, wherein the mutant hERα has a DBD, a LBD, and an interface between the DBD and the LBD, and wherein at least one tryptophan residue is mutated to a phenylalanine residue, and monitoring the change in tryptophan fluorescence of the mutant hERα. The tryptophan fluorescence of the mutant hERα can be monitored using a fluorescence assay protocol as described below. In some instances, a decrease in tryptophan fluorescence as compared to a control indicates that the therapeutic agent binds to the mutant hERα. In other instances, an increase in tryptophan fluorescence as compared to a control indicates that the therapeutic agent binds to the mutant hERα.

Another aspect of the present disclosure can include a fluorescence assay protocol for use in monitoring tryptophan fluorescence of the mutant hERα. In one aspect, the fluorescence assay can include a mutant hERα as described herein. The fluorescence assay can also include the use of one or more protein buffers. Additionally, the fluorescence assay can include the use or screening of potential therapeutic agents that may bind the mutant hERα.

The protein buffer can include components generally found in a protein buffer. In one instance, the protein buffer can contain one or more of CHES, KCl, NaCl, $MgCl_2$, arginine, glutamic acid, TCEP, glycerol, and ZnCl. In certain instances the protein buffer can include a therapeutic agent known to bind to hERα. In some instances, the therapeutic agent can be estradiol or derivatives thereof. In other instances, the therapeutic agent can be an estrogen receptor down-regulator such as fulvestrant. In further instances, the therapeutic agent can be a selective estrogen receptor modulator, such as tamoxifen or toremifene. In one particular instance, the therapeutic agent is estradiol.

Potential therapeutic agents that may bind a mutant hERα can include small molecule compounds, including small molecule drugs, nucleic acids (e.g., siRNA, aptamers, short hairpin RNAs, antisense oligonucleotides, ribozymes, antagomirs, microRNA mimics or DNA) or polypeptides, e.g., antibodies (e.g., full length antibodies or antigen-binding fragments thereof, Fab fragments, or scFv fragments).

The intrinsic fluorescence of the tryptophan residues present at the DBD-LBD interface of the mutant hERα can be probed using methods known in the art. For example, a spectrofluorometer can be used to measure the tryptophan fluorescence of the mutant hERα. Other methods for measuring tryptophan fluorescence include fluorescence microscopy, fluorescence polarization, fluorescence scanners (including microarray readers), and flow cytometers. When a spectrofluormeter is used, emission spectra may be recorded, for example, between 310 and 400 nm with a bandwidth of 5 nm and excitation at 295 nm.

In one aspect, the following exemplary fluorescence assay protocol can be used to monitor tryptophan fluorescence of the mutant hERα. The assay components can include a mutant hERα as disclosed herein, a protein buffer, and a therapeutic agent that may bind the mutant hERα. First, a baseline fluorescence measurement can be taken of the protein buffer. Second, the therapeutic agent can be combined with the buffer to create a therapeutic agent solution, and the emission spectrum of the therapeutic agent solution can be recorded. The emission spectrum of the therapeutic agent solution can be analyzed to ensure that the therapeutic agent does not have an absorption peak at the excitation wavelength. Third, the mutant hERα can be combined with the buffer solution to create a mutant hERα/buffer solution, and an initial emission spectrum can be recorded of the mutant hERα/buffer solution. The mutant hERα may be present in the solution at a concentration of for example, 0.05-3.0 mg/mL. Fourth, the mutant hERα/buffer solution can be titrated by successive additions of the therapeutic agent solution. Following each addition of the therapeutic agent solution the fluorescence spectrum can be recorded. The entire solution can be incubated for a designated amount of time, e.g., 30 minutes, following each addition of the therapeutic agent solution. Sixth, the therapeutic agent solution can be added to the mutant hERα/buffer solution until the fluorescence intensity saturates.

The collected florescence data can then be corrected for contribution of the buffer. The relative fluorescence quenching intensity can be calculated using the following formula:

$$\frac{F_0 - F}{F_0}$$

$F_0$-F can be represented by $\Delta F$. $F_0$ is the fluorescence intensity of the mutant hERα only, and F is the fluorescence intensity of the mutant hERα titrated with the therapeutic agent.

A therapeutic agent binding analysis can be carried out using the Hill equation.

$$\frac{\Delta F}{\Delta F \max} = \frac{1}{[1 + (Kd/X)^n]}.$$

$\Delta F$ max is the saturating value of fluorescence change, X is the therapeutic agent concentration, Kd is the dissociation constant, and n is the Hill coefficient.

In some instances, a decrease in tryptophan fluorescence as compared to a control indicates that the therapeutic agent binds to the mutant hERα. In other instances, an increase in tryptophan fluorescence as compared to a control indicates that the therapeutic agent binds to the mutant hERα.

V. Kits

Another aspect of the present disclosure can include a kit that contains a mutant hERα, as described herein, at least one protein buffer, and instructions for using the kit to carry out a method of drug discovery.

The kit can also include other necessary components, such as solvents, stabilizers, and preservatives.

The mutant hERα can be provided in any form, e.g., liquid, dried, semi-dried, or lyophilized, or in a form for storage in a frozen condition.

In one instance, the mutant hERα and other components in the kit can be provided in a form that is sterile. For example, when the mutant hERα is provided in a liquid solution, the liquid solution can be a sterile solution. When the mutant hERα is provided in a dried form, reconstitution can be accomplished by the addition of a suitable sterile solvent. The solvent, e.g., a sterile buffer, can optionally be provided in the kit.

The kit can include one or more containers, dividers or compartments (herein referred to as "containers") for the components included in the kit. For example, the kit can include a container that comprises a mutant hERα and one or more protein buffers. The kit can also include a separate container for the protein buffer. In one instance, one or more protein buffer components can be in separate containers. In some instances, the kit can contain separate containers for the mutant hERα, the protein buffer, and the informational material. For example, the mutant hERα can be contained in a bottle or vial, the protein buffer can be contained in a bottle or vial, and the informational material can be contained in a plastic sleeve or packet. In other instances, the kit components can be contained within a single, undivided container. For example, a mutant hERα and the protein buffer can be contained in a bottle or vial that has attached thereto the informational material in the form of a label.

The containers can be, for example, vials, ampoules, foil packets, or blister packs. The containers of the kits can be air tight and/or waterproof. The container can be labeled for use.

The kit can include informational material for performing and interpreting a method of drug discovery. In one example, the instructions can include a method of drug discovery as described above. The kit can include forms for reporting the results of the method of drug discovery and contact information regarding where to send such forms or other related information; or a URL (Uniform Resource Locator) address for reporting the results in an online database or an online application (e.g., an app).

The informational material of the kits is not limited in its form. In many cases, the informational material, e.g., instructions, can be provided in printed form, e.g., a printed text, drawings, and/or photographs, e.g., a label or a printed sheet. However, the informational material can also be provided in other formats, such as computer readable forms, video recordings, or audio recordings. In another instance, the informational material can include contact information, e.g., a physical address, email address, website, or telephone number, where a user of the kit can obtain substantive information about the method of drug discovery and/or its use in the methods described herein. The informational material can also be provided in any combination of formats.

VI. Experimental

The following Example is for the purpose of illustration only is not intended to limit the scope of the appended claims.

Example 1

This Example discloses the methods used to both elucidate the complete structure of hERα and to characterize the hERα domain interactions. The Example also details how the hERα domain interactions can be used to develop a method for structure-based drug discovery.

Methods
Domain Interaction

Activated by its cognate hormone estradiol, hERα functions as a homodimer and regulates transcription by binding specific DNA sequences in target genes. Like other NRs, it contains a highly conserved DBD and a C-terminal 12-helical LBD (FIG. 6a).

Current understanding of the mechanistic action of hERα has mostly relied on analyses of the individual DBDs or LBDs. For example, the crystal structure of the DBD homodimer shows that the DBD binds a consensus palindromic DNA duplex known as estrogen response element (ERE) (FIG. 6b), while the LBD homodimer in complex with estradiol and coactivator TIF2 peptides shows that the hormone is capped in place by its C-terminal helix H12 (FIG. 6c). For other NRs, solution-phase biophysical techniques, including small-angle X-ray scattering (SAXS), fluorescence resonance energy transfer, and H/D exchange, have provided various levels of structural information for complexes including RXRα-RARa and VDR-RXRα. One recent structural study of hERα using cryo-electron microscopy (EM) showed hERα in complex with coactivators within a large transcription complex, although this EM study at a 22-Å resolution did not provide a detailed picture of the DBD-LBD architecture. Computational docking studies of individual hERα domains have revealed a variety of likely hERα structures, but the selection of reliable conformations has remained speculative due to the lack of experimental support, pointing to the need for a molecular understanding of the hERα complex and its domain interactions.

To investigate how the different domains within the hERα interact with each other, multiple highly complementary, in-solution biophysical studies using a recombinant active form of the hERα protein were conducted. To identify specific sites of domain interaction, a hydroxyl radical-based protein footprinting was used, where hydroxyl radicals (generated by radiolysis) react with solvent accessible side chains and the sites and rates of oxidation are monitored by quantitative mass spectrometry (MS). The resultant data provide a measure of surface accessibility of individual residue side chains. Two separate clusters of hydrophobic residues were identified that are on the surface of each of the domain-dimers in the isolated states (as seen from their crystal structures), but are much less solvent accessible in the examination of the complex.

To investigate the overall domain arrangement, SAXS data of the complex in solution was acquired, thereby enabling the complementary integration of SAXS data with residue-level information from footprinting to elucidate the hERα DBD-LBD architecture and identify a network of residue-residue interactions at the DBD-LDB interface. The findings were validated by employing site-directed mutagenesis followed by functional transcriptional and DNA-binding studies. Investigation was also undertaken to see if the mutations can influence the structural stability across the interface to a distal domain, using intrinsic tryptophan fluorescence. The observation that interfacial mutations alter the hERα structure and function establishes the existence of a previously uncharacterized interaction between the DBD and LBD, and further demonstrates the functional relevance of the DBD-LBD interface. Notably, the L-shaped boot structure of the receptor represents a distinctive architecture of the DBD-LBD spatial organization that can be used to interpret the functional relation of clinical mutations and provides a structural basis for developing small molecules by disrupting the cross-talk at the DBD-LBD interface to regulate receptor function.

Specific Residue Sites Involved in DBD-LBD Contact

A multidomain segment of the hERα containing both DBD and LBD (residues E181-P552 (SEQ ID NO: 9) (FIG. 7), referred to as hERα$^{CDE}$ in FIG. 6a) was generated. The hERα$^{CDE}$ proteins were purified using size exclusion chromatography (FIG. 8), in the presence of the receptor's ligands: E2, an ERE-containing DNA duplex (ERE-DNA; 5'-TAGGTACACGTGACCTGCG-3' (SEQ ID NO: 10) and 5'-CGCAGGTCACTGTGACCTA-3' (SEQ ID NO: 11)), and a coactivator TIF2 peptide (KENALLRYLLDKDD) (SEQ ID NO: 12). Hereinafter this is refered to this as hERα$^{complex}$. Purified hERα$^{complex}$ samples at micromolar concentrations were exposed to a focused synchrotron X-ray white beam, the sites of oxidation were detected by tandem MS (MS/MS), and the extent of modification was quantified as a function of X-ray dose (see examples in FIG. 9). These curves were fit to an exponential decay function and the measured rate constants (kfp) were divided by a measure of their intrinsic reactivity with hydroxyl radicals (kR), thereby providing a residue-level protection factor (PF=kR/kfp). The log of the PF values provides an accurate surface topology map, where high log PF values reflect more protection for solvent and lower log PF values reflect greater solvent exposure for the set of 20-probed residues across the receptor (FIG. 6d), as reflected by the correlation between log PF and solvent accessibility of the hERα residues (FIG. 6f).

The measured log PF values for the 20 residues (FIG. 6d) were compared with their solvent accessible surface areas (SA) extracted from the crystal structures of their individual domain-dimers (FIG. 6e). The expectation was that residues involved in the interface are expected to have large SA values as in the isolated domains, but also have high log PF values (i.e., be solvent-protected) in the complex. For the ten most solvent-exposed residues for the isolated domain structures (with SA values ranging from 45.9 to 147.6 Å2), only six exhibit high log PF values (ranging from −0.39 to 2.13) for the hERα$^{complex}$ (red stars, FIG. 6d). In contrast, other highly protected residues among the 20, like M343, Y197, M315, F208, and L408 (log PF=−0.31, −0.26, −0.03, 0.64, and 1.25, respectively) have SA values from crystallography of less than 15 Å2 (Table 1), indicating that they are protected for the individual domains as well as the observed complex. The differentiation of the six from the remaining 14 residues is also demonstrated by examining the relationship of log PF and SA for the 14 residues. The Pearson's correlation coefficient, p=−0.77 (p-value=0.001) (black dots in FIG. 6f), suggests that the observed log PF values for these residues are consistent with the isolated domain structures, while the six suggested contact residues show a significant departure from the fit line and an overall inconsistency with the individual domain structures. Other residues highly exposed for the individual domains (e.g., M220 and M437) remain fully solvent-exposed in the complex (log PF=−3.33 and −3.78, respectively), ruling them out as candidates for the interface as well.

TABLE 1

| | Residue | $k_{fp}$ (s$^{-1}$) | logPF | SA (Å$^2$) | SA$^{fit}$ (Å$^2$) |
|---|---|---|---|---|---|
| Control (14) | H196 | 123.30 ± 3.31 | −2.59 ± 0.03 | 18.0 | 44.2 |
| | H197 | 15.48 ± 0.87 | −0.26 ± 0.06 | 4.5 | 13.4 |
| | F208 | 5.94 ± 0.51 | 0.64 ± 0.09 | 0.1 | 1.6 |
| | M220 | 575.30 ± 13.90 | −3.33 ± 0.02 | 45.0 | 54.1 |
| | M315 | 21.17 ± 0.98 | −0.03 ± 0.05 | 2.3 | 10.4 |
| | P325 | 4.29 ± 0.25 | −1.46 ± 0.06 | 48.5 | 29.2 |
| | M343 | 28.01 ± 1.23 | −0.31 ± 0.04 | 6.7 | 14.1 |
| | M357 | 66.64 ± 6.02 | −1.18 ± 0.09 | 12.0 | 25.6 |
| | L408 | 1.26 ± 0.05 | 1.25 ± 0.04 | 7.4 | −6.6 |
| | M427 | 118.51 ± 6.97 | −1.75 ± 0.06 | 29.5 | 33.2 |
| | M437 | 895.60 ± 74.28 | −3.78 ± 0.08 | 69.6 | 59.9 |
| | K492 | 4.87 ± 1.80 | −0.79 ± 0.37 | 32.0 | 26.0 |
| | L495 | 55.16 ± 2.74 | −2.53 ± 0.05 | 50.3 | 43.4 |
| | L497 | 30.21 ± 4.29 | −1.92 ± 0.14 | 72.8 | 35.4 |
| Prediction (6) | Y191 | 11.50 ± 0.53 | 0.04 ± 0.05 | 147.6 | 9.5 |
| | Y195 | 17.80 ± 0.70 | −0.39 ± 0.04 | 104.1 | 15.2 |
| | W200 | 2.05 ± 0.11 | 2.14 ± 0.05 | 106.1 | −18.3 |
| | I326 | 1.64 ± 0.19 | 0.99 ± 0.12 | 77.7 | −3.0 |
| | W393 | 7.15 ± 0.76 | 0.89 ± 0.11 | 73.4 | −1.8 |
| | L409 | 1.24 ± 0.03 | 1.27 ± 0.02 | 45.9 | −6.8 |

The footprinting rates (k$_{FP}$) and protection factors (log PF) for individual residues probed by footprinting. The twenty residues were divided into two groups. The first group is the control set of 14 residues that were used for linear regression and the second group includes six residues with large changes in logPF and SA values. SA values were calculated from the domain structures. The SA$^{fit}$ values are the theoretical estimates inferred from the linear fit, where negative SA$^{fit}$ values suggest that they are not solvent-exposed in the complex.

Of the six candidate residues, W200 is fully exposed in the crystal structure of the DBDs (SA=106.1 Å$^2$), while it has the highest log PF value (log PF=2.14) for hERα$^{complex}$, a strong evidence that it is highly buried within DBD-LBD contacts. Similarly, I326 and W393 experience a notable change in solvent accessibility with relatively high log PF values in the complex (log PF=0.99 and 0.89, respectively), but are fully solvent exposed on the individual domain surface (SA=77.7 and 73.4 Å$^2$, respectively). From a quantitative perspective, the relationship of FIG. 6f can be used to infer the SA values for the six putative interfacial residues in hERα$^{complex}$, suggesting the six residues experience SA decrease ranging from 53 Å$^2$ (L409) to 157 Å$^2$ (Y191) for the complex, compared to their SA values in the individual domains (Table 1).

Consistent with these residues participating in the architecture of the interface, these residues define two separate hydrophobic clusters in the hERα$^{complex}$. One hydrophobic cluster is formed among residues Y191, Y195, and W200 on the DBD surface (FIG. 6g), and the other is on the LBD including I326, W393, and L409 (FIG. 6h). Overall, the observed high log PF values of these hydrophobic residues coupled with the fact that they are solvent exposed on the domains' surfaces and their clustering as patches on the LDB and DBD all point to their involvement in DBD-LBD interactions. H, the mode of interaction between the domains is not clear from the footprinting data alone.

Overall Architecture of the Homodimeric hERα Complex

Figure 10:
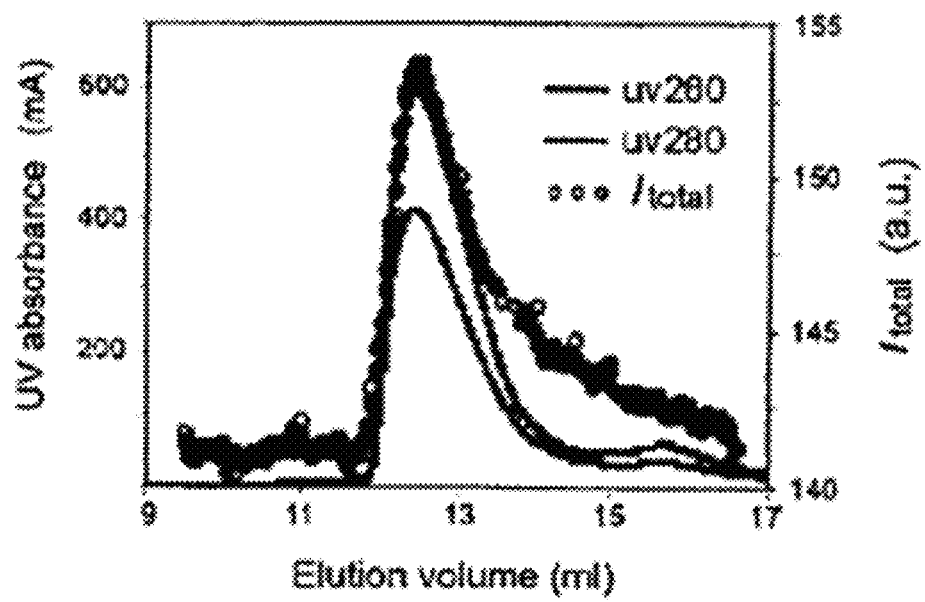
FIG. 10 shows chromatography-coupled SAXS data acquisition of hERα. UV absorbance and total scattering intensity are shown along the y-axes, and size exclusion chromatography (SEC) elution of hERα$^{comPlex}$ is shown along with x-axis. The total scattering intensity, $I_{total}$, was calculated by integrating all scattering signals over the entire q-range (up to 0.3 Å$^{-1}$).

To investigate the actual domain arrangement between the DBD and LBD, small-angle X-ray scattering (SAXS) data of the hERα$^{complex}$ in solution was acquired. SAXS provides structural information about spatial organization of the domains. By using the elution peak of purified hERα$^{CDE}$ proteins in the presence of the receptor's ligands, an "on-the-fly" SAXS data acquisition was achieved for the hERα$^{complex}$ via a chromatography-coupled setup (FIG. 10). This approach mitigates potential protein aggregates and contamination from excess ligands. The ab initio SAXS reconstruction alone has been successfully applied to visualize the overall shapes of several NR complexes. By combining domain-arrangement data from SAXS with protector factors of surface residues from footprinting, a detailed and reliable picture for hER$\alpha^{complex}$ can be constructed. This experiment-directed integrative approach has proven valuable in overcoming the limitations of individual techniques, in this case suitable for elucidating the hER$\alpha$ structure.

Figure 11:
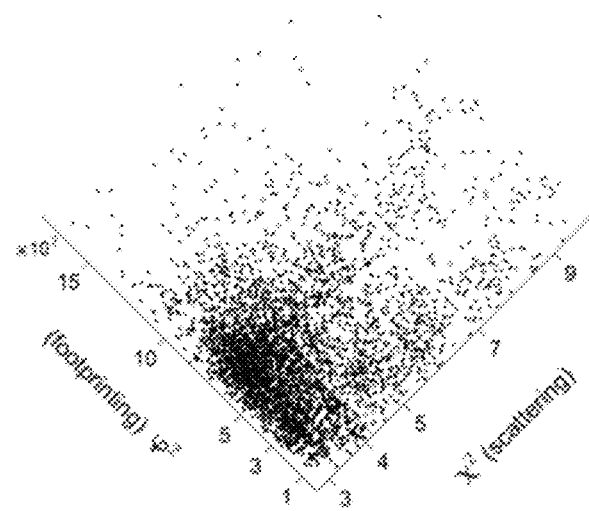
FIG. 11 shows a graph of data integration by fitting docking results against experimental data. The fit of computationally generated conformations (dot) is simultaneously assessed against footprinting ($φ2$) and scattering ($χ2$).

To determine the three-dimensional organization and structure of hER$\alpha$, computational docking models were scored against experimental SAXS (domain arrangement) and footprinting (contact site) data via an in-house multi-technique iSPOT platform. Computationally docked structures were generated in two steps of (1) rigid-body docking and coarse-grained sampling, and (2) atomic-level simulations with distance restraints between the two clusters Y191/Y195/W200 and I326/W393/L409 (Methods). The former sampling was among rotational and translational motions between the domains (i.e., five initial poses per rotation and a range of 0-50 Å for translation) to achieve an extensive search, while the latter atomic-level simulations were distance restrained linearly from 2 to 10 Å between the centers of mass of the two clusters to concentrate on local sampling. The goodness of fit of each structural candidate against the experimental SAXS and footprinting data was evaluated via two scoring functions $\chi^2$ and $\varphi^2$. The unit-less $\chi^2$ is defined to measure the difference between the theoretical and experimental SAXS profile by, $$\chi^2 = \frac{1}{N_q}\sum_q \frac{\{\log I_{cal}(q) - \log I_{exp}(q)\}^2}{\sigma^2(q)}, \quad (1)$$

where $I_{cal}$ is calculated using fast-SAXS-pro[35] and $N_q$ is the number of scattering q points recorded in experimental $I_{exp}$ (with its measurement error of $\sigma(q)$). Similarly, the $\varphi^2$ is the goodness of fit between experimental and theoretical footprinting data by, $$\varphi^2 = \frac{1}{N_s}\sum_s \frac{\{\log PF_{cal}(s) - \log PF_{exp}(s)\}^2}{\delta^2(s)}, \quad (2)$$

where log $PF_{cal}$ is the predicted log PF value of each site based on its corresponding SA value, using the linear regression between experimental log $PF_{exp}$ values (with an error $\delta(s)$ at each site (s)) and SA values of $N_s$ sites for each docked structure. The precise evaluation by $\chi^2$ and $\varphi^2$ enables the differentiation among all docked structural candidates (FIG. 11), i.e., a lower $\chi^2$ and $\varphi^2$ value indicates a better fit with experimental scattering and footprinting data at the domain arrangement and local contact-site level (FIG. 12a), respectively. This permits the identification of the best-fit ensemble structures (FIG. 12b, c) that fit both scattering and footprinting data simultaneously. The latter are within 3 Å of C$\alpha$-RMSD from the former best-fit structure (FIG. 13).

Figure 12:
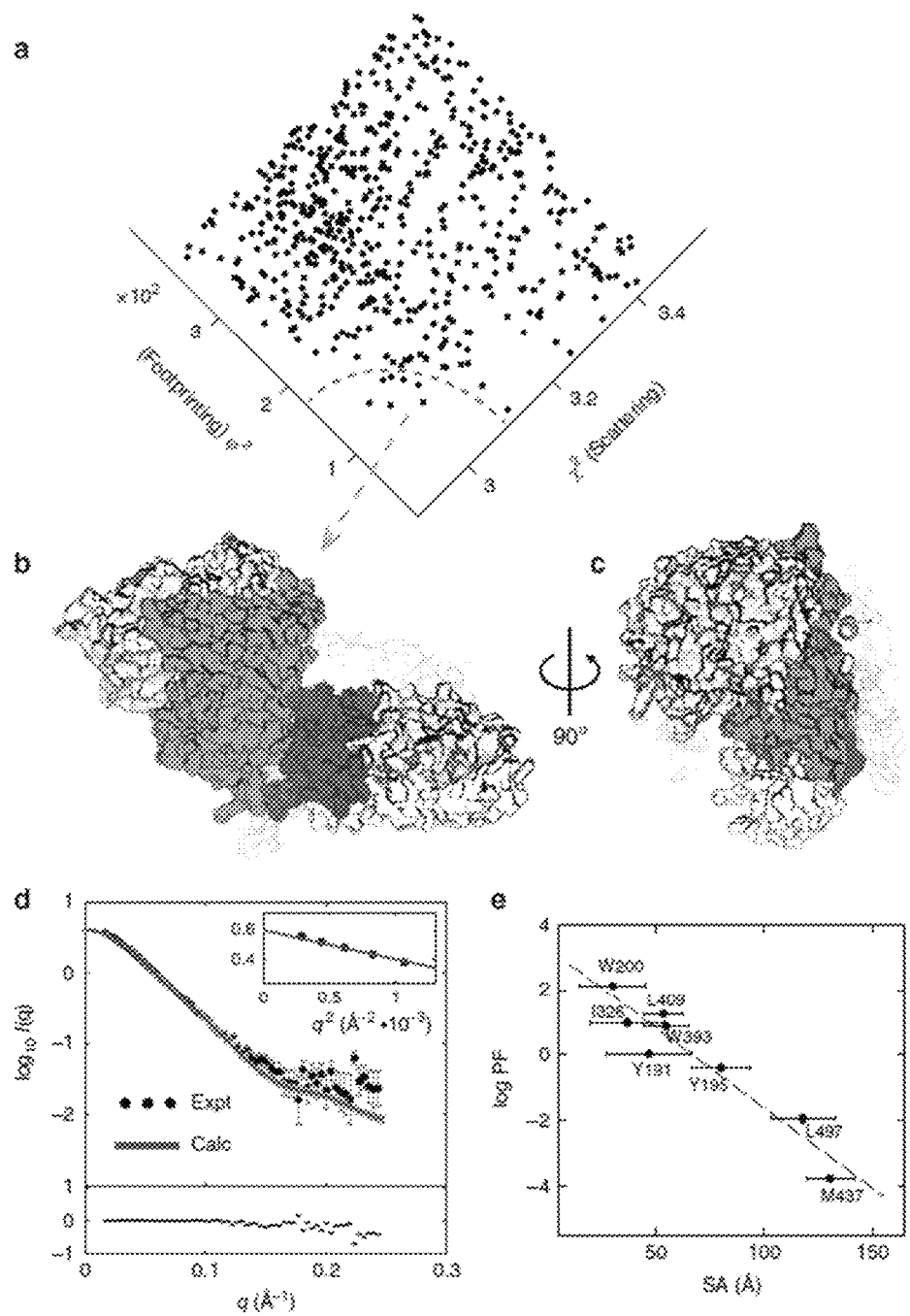
FIGS. 12(a)-(e) show the overall architecture of the hERα homodimer revealed by data integration.

Overall, the multidomain hER$\alpha$ exhibits an asymmetric organization that resembles an asymmetric L-shaped "boot" (FIG. 12b, c). One of the LBDs leans against its own DBD (at the "tongue" position of the boot) with its interacting ERE-DNA below (the "outsole" position), while the LBD dimer form the boot "shaft" and lie perpendicular to the plane of the DBD dimer and the ERE-DNA. Based on the observed ensemble structures (FIG. 12b), a large C$\alpha$-atom RMS fluctuation (C$\alpha$-RMSF) is observed at the domain-connecting region ranging from 5 to 10 Å, although most tertiary domains and footprinting-detected residues have a C$\alpha$-RMSF value of around 2-4 Å (FIG. 14). This large fluctuation at the domain-connecting region makes its placement with respect to the DBD and LBD less certain. It should be noted that it is possible to have large flexibility with the loop region (e.g., in a C$\alpha$-RMSF range of 10-30 Å) (FIG. 15a), although its contribution to overall scattering is relatively small with the overall $\chi^2$=1.2±0.1 (FIG. 15b), where the large structural fluctuation in the loop (with a RMSD value up to 23 Å) contributes <10% to the overall $\chi^2$ value of the entire complex. While it appears that the LBD interacts with DBD within the same polypeptide chain, the possibility that the DBD and LBD are each from a different polypeptide chain (e.g., domain swapping) could not be excluded, despite the strong binding between the LBD monomers within its dimeric complex as well as strong interactions of the DBD dimer with the ERE-DNA duplex. It also appears that modest conformational deformation occurs in the LBD-DBD interface upon complex formation, compared to the crystal structures of individual domains, especially for the DBD contact residues (FIG. 16).

The goodness of fit of the hER$\alpha$ ensemble structures is evidenced by the agreement between experimental and calculated scattering and footprinting data. Comparison of the calculated and experimental SAXS profile yields $\chi^2$=3.0±0.1 (using fast-SAXS-pro[35]), and an even better score $\chi^2$=1.2±0.1 (using CRYSOL[36]) (FIG. 12d). Based on the same ensemble structures, the average SAs are linearly correlated with their corresponding measured log PF values at a correlation coefficient −0.95 (p-value=0.002) for the observed sites (FIG. 12e). Whereas an absolute measure of model resolution is not apparent from the goodness of fit, the C$\alpha$-RMSD of the hER$\alpha$ ensemble structures provides a reliable description (using one of its own best-fit structures as a reference), with regard to the final models' accuracy (FIG. 13). In addition, the prior theoretical study using simulated scattering and footprinting data of the structurally known HNF-4$\alpha$ homodimer, similar to hER$\alpha$ in size, predicted a very close RMSD value of 4.2 Å (excluding domain-connecting loop regions), compared to its solved crystal structure. Notably, the observed hER$\alpha$ domain arrangement within its boot-like architecture fits qualitatively into the EM map at a 22-Å resolution (EM Data Bank EMD-8832) of the full-length hER$\alpha$ (FIG. 17). Taken together, this consistency nicely affirms the positioning of the observed asymmetric domain arrangement.

The DBD-LBD Interface and its Functional Importance

The observed domain arrangement and mode of interaction between the DBD and LBD warranted a residue-residue contact analysis at the DBD-LBD interface. By examining the molecular surfaces that interact with one another using the contact of structural units (CSU) approach, a well-formed interface was observed between the DBD and LBD (FIG. 18a). The interface is mainly composed of hydrophobic contacts (FIG. 18b), between the DBD's residues, including Y191, Y195, G198, V199, and W200 right before the first helix of the DBD and the LBD's eight contact residues, including I326, Y328, W393, E397, L403, P406, N407, and L409. Using the conventional hER$\alpha$-LBD nomenclature (FIG. 19), it was found that the LBD contact residues are positioned in the two-strand region between helices H5 and H6 (L403/P406/N407/L409), the end of helix H5 (W393), and the loop region between helices H1 and H3 (I326/Y328). A close-up view shows a modest-sized pocket on the LBD surface in contact with the DBD (FIG. 20), where residue W200 becomes buried and protected from solvent exposure at the interface, consistent with its lack of radiolytic labeling (FIG. 9) and its high protection factor (FIG. 6d).

The functional importance of the DBD-LBD interface was first explored by introducing mutations at this domain-domain junction and analyzing their effects on transcriptional activity. The introduction of point mutations on the LBD, namely, I326A, Y328A, P406A, and L409A (FIG. 21a), considerably reduced the transcriptional activity when compared to the wild-type protein (FIG. 21b). Additionally, Gal4-DBD/hERα-LBD fusion proteins were generated for both wild-type and mutant hERα-LBD, and it was found that these mutant fusion proteins possess comparable E2-induced reporter activity to that of the wild-type hERα-LBD (FIG. 21c). These results argue against the possibility that these hERα-LBD mutants lose their hormone or coactivator-binding activities, further confirming the functional significance of these interfacial residues in mediating the receptor's transcriptional function through the LBD-DBD interface. Interestingly, mutations at these sites, such as I326, P406, and L409, have been identified in cancer patient samples. While their oncogenic relevance remains to be established, alteration of the DBD-LBD interface by these mutations on reporter activity may provide a functional link to their ability to regulate transcription.

Notably, the substitution of a non-charged residue Y191 with a charged histidine resulted in increased transcriptional activity (FIG. 18c). From a structural perspective, the Y191H mutation likely resulted in a local energetic stabilization due to a stronger interaction with its oppositely charged neighbor residue, E397, across the interface. To further assess the impact of this substitution on the receptor's ability to bind ERE-DNA, a biochemical DNA-binding assay was performed by detecting fluorescence anisotropy of 6-carboxyfluorescein-labeled ERE-DNA in the presence of increasing concentrations of the E2-bound hERα$^{CDE}$. The assay was applied to WT, W393A, and Y191H conditions, respectively, to obtain their DNA-binding affinity $K_d$ values (Methods). As a negative control, W393A had little change concerning its DNA-binding affinity $K_d$=10.8 nM, compared to the WT's $K_d$=9.2 nM (FIG. 8d), whereas Y191H increased the binding affinity about threefold to $K_d$=3.2 nM (FIG. 22). Interestingly, this Y191H mutation has also been observed in endometrial cancer samples. While its oncogenic function is unknown, it should be noted that the structural role of Y191H with its energetic stabilization of the DBD-LBD interface correlates with increased DNA binding and with elevated transcriptional activity in vitro that may occur in cancer patients.

Finally, the potential mutational influence on the observed domain-domain interface itself was directly tested. The residue N407, part of the hydrophobic cluster among N407, Y195, and W200 at the interface (FIG. 18d), was mutated into alanine to alter the interfacial structure. The effect of N407A on transcriptional activity was evaluated again by transient transfection reporter assays. In contrast to the Y191H mutation noted above, which increased reporter luciferase activity, the N407A mutation decreases E2-induced reporter activity using both an ERE-TK-Luc and a Gal4-TK-Luc reporter construct (FIG. 18c and FIG. 23). Its impact on the interfacial structure was further assessed by tryptophan fluorescence of W200, also part of the domain interface. It should be emphasized that N407 and W200 are each situated on different domains of the complex. As such, the extent of W200 exposure at the interface—as observed and noted above—is especially critical because the disruption by the N407 Å mutation would alter the W200 surroundings and reflect the local conformational changes occurring at the domain interface, influencing its emission spectra (FIG. 18e), and thus provide a direct confirmation of domain interaction.

By mutating four other tryptophan residues into phenylalanine and keeping W200 untouched in the hERα$^{complex}$, this genetically engineered construct for tryptophan fluorescence measurements was able to be utilized to monitor changes to the interfacial structure of W200's surroundings resulting from structural perturbation. A significant decrease was observed in the fluorescence emission spectra for mutant N407 Å with a peak reduction of about 30% (FIG. 18f). Of note, residue N407 in the structure places the LBD in close contact with W200 of the DBD across the DBD-LBD interface. The reduction in W200 fluorescence in the context of the N407 Å substitution confirms the observed DBD-LBD interface as necessary for maintaining the appropriate domain interaction and its influence in modulating transcriptional luciferase activity.

The L-shaped boot architecture of hERα complex reported here represents a distinctive spatial arrangement between the DBD and LBD among members of the NR superfamily (FIG. 24a). As schematically illustrated (FIG. 25), comparison with existing NR crystallographic or cryo-EM structures shows that hERα$^{complex}$ adopts a different domain organization from currently known NR architectures such as an elongated PPARγ-RXRα and an italicized-X-like RXRα-LXRβ (FIG. 25c). The spatial difference is reaffirmed by their structural incompatibility with the experimental scattering data of hERα$^{complex}$, where theoretical SAXS profile of each known NR structure, after threading the hERα sequence (with the ligands kept untouched), yielded a large discrepancy in $\chi^2$ with the experiential scattering data of hERα$^{complex}$ (FIG. 26a). At the domain level, a pronounced difference among these NR complexes is indicated by their buried domain surface areas of the LBDs involved in DBD-LBD interactions, with 1219 Å$^2$ for PPARγ-RXRα, 562 Å$^2$ for RXRα-LXRβ, while here 747 Å$^2$ was calculated for hERα (FIG. 26b), pointing to a distinguishable contact interface formed between the hERα-DBD and LBD that is distinct from the others. It should be noted that hERα resembles the extended conformation that USP/EcP adopts, although the way individual domains are assembled to interact is different. Specifically, hERα-LBD and -DBD directly interact (FIG. 25a), while USP/EcP LBD interacts with DNA instead (FIG. 25b). Overall, the L-shaped boot architecture of the hERα and the allosteric path through the previously unknown DBD-LBD contact presents a distinctive DBD-LBD spatial organization within the NR superfamily.

The functional importance of hERα DBD-LBD contact, based on a favorable interaction between its LBD hydrophobic patch surrounding its two β-strands between helices H5 and H6 (FIG. 24b and FIG. 19) is fully supported by the observation that interfacial mutations (e.g., Y191H) alter the receptor's ability to regulate transcription as well as its ability to bind DNA. Of note, a similar β-strand region is also involved in PPARγ-RXRα's domain—domain interactions, where residue F347 from the H5-H6 connecting β-strand region of PPARγ-LBD is shown to functionally mediate its DBD-LBD interface, despite an apparent difference from the solution structure. It can be noted that the use of the β-strand region is distinctive for hERα and PPARγ-

RXRα, departing from other NR complexes such as RARβ-RXRα and HNF-4α that use a different region near helices H9 and H10 for domain—domain interactions. Strikingly, mutations at the LBD hydrophobic patch, residues I326A, Y328A, P406A, and L409A from the β-strand region, significantly inhibited E2-induced transactivation without reducing their capability of hormone and coactivator binding (FIG. 21b-c). Moreover, the structure-function studies find that the hERα DBD-LBD couplings involving the patches in these locations allow for effective signal transmission from the LBD to the DBD. In particular, the DBD-LBD junction allows information about the N407 Å mutation at the LBD to be allosterically transduced to W200 (FIG. 18f) at the DBD by influencing its surroundings at the interface, as reflected in the reduction of tryptophan fluorescence. As such, alteration of interfacial structures, e.g., by point mutations such as N407A, can be probed via intrinsic tryptophan fluorescence using a genetically engineered hERα construct (depicted in FIG. 24c). In principle, this fluorescence assay can be used to monitor the disruption of the hERα DBD-LBD interface due to binding of novel small molecules, especially because of the increasing importance of drug targeting at protein—protein interfaces. The modulation of the DBD-LBD interface as an "allosteric" channel of hERα with gain or loss of receptor function—going beyond the current focus on the "active" site of estradiol binding—is crucial to the articulation of signaling across the interface and for providing a molecular understanding of the inner-workings of receptor activation.

Methods

Recombinant Expression and Purification

The human ERα segment containing both the DNA-binding and ligand-binding domain (amino acids 181-552 (SEQ ID NO: 13) (FIG. 27), referred to as hERα$^{CDE}$) was expressed in *E. coli* cells in the presence of estradiol (E2). The purified hERα protein was incubated with E2, ERE-DNA (5'-TAGGTACACGTGACCTGCG-3' (SEQ ID NO: 14) and

5'-CGCAGGTCACTGTGACCTA-3'(SEQ ID NO: 15))

and a coactivator TIF2 peptide (KENALLRYLLDKDD) (SEQ ID NO: 16) as adopted in the crystal structures available in the literature (Schwabe et al., Cell, 75: 567-78 (1993); Warnmark et al., J. Biol. Chem., 277: 21862-68 (2002); Gangloff et al., Biol. Chem., 276: 15059-65 (2001)) referred to as hERα$^{complex}$. The hERα$^{CDE}$ was cloned into pMCSG7 vector. The primer sequences related to cloning and mutagenesis are shown in Table 2.

TABLE 2

Primer sequences used for hERα constructs

| Construct | Forward Primer | Reverse Primer |
|---|---|---|
| hERα$^{CDE}$ | 5'-GGTGAATTCGAGACTCGCTACTGTGC-3' (SEQ ID NO. 17) | 5'-ATTGGATCCTCAGGGCGCATGGATGG-3' (SEQ ID NO: 18) |
| Y191H | 5'-GTGCAGTGTGCAATGACCATGCTTCAGGCTACCATTATG-3' (SEQ ID NO: 19) | 5'-GACATAATGGTAGCCTGAAGCATGGTCATTGCACACTGCAC-3' (SEQ ID NO: 20) |
| I326A | 5'-TTGGATGCTGAGCCCCCCGCACTCTATTCCGAGTATGAT-3' (SEQ ID NO: 21) | 5'-ATCATACTCGGAATAGAGTGCGGGGGGCTCAGCATCCAA-3' (SEQ ID NO: 22) |
| Y328A | 5'-GCTGAGCCCCCCATACTCGCTTCCGAGTATGATCCTACC-3' (SEQ ID NO: 23) | 5'-GGTAGGATCATACTCGGAAGCGAGTATGGGGGGCTCAGC-3' (SEQ ID NO: 24) |
| P406A | 5'-GTGAAGCTACTGTTTGCTGCTAACTTGCTCTTGGACAGG-3' (SEQ ID NO: 25) | 5'-CCTGTCCAAGAGCAAGTTAGCAGCAAACAGTAGCTTCAC-3' (SEQ ID NO: 26) |
| N407A | 5'-AAGCTACTGTTTGCTCCTGCCTTGCTCTTGGACAGGAAC-3' (SEQ ID NO: 27) | 5'-GTTCCTGTCCAAGAGCAAGGCAGGAGCAAACAGTAGCTT-3' (SEQ ID NO: 28) |
| L409A | 5'-CTGTTTGCTCCTAACTTGGCCTTGGACAGGAACCAGGGA-3' (SEQ ID NO: 29) | 5'-TCCCTGGTTCCTGTCCAAGGCCAAGTTAGGAGCAAACAG-3' (SEQ ID NO: 30) |
| W272F | 5'-GAGCTGCCAACCTTTTCCCAAGCCCGCTCATG-3' (SEQ ID NO: 31) | 5'-CATGAGCGGGCTTGGGAAAAGGTTGGCAGCTC-3' (SEQ ID NO: 32) |
| W360F | 5'-GGTTCACATGATCAACTTCGCGAAGAGGGTGCCAG-3' (SEQ ID NO: 33) | 5'-CTGGCACCCTCTTCGCGAAGTTGATCATGTGAACC-3' (SEQ ID NO: 34) |

TABLE 2-continued

Primer sequences used for hERα constructs

| Construct | Forward Primer | Reverse Primer |
|---|---|---|
| W383F | 5'-CACCTTCTAGAATGTGCCTTCCTAGAGATCCTGATGATTG-3' (SEQ ID NO: 35) | 5'-CAATCATCAGGATCTCTAGGAAGGCACATTCTAGAAGGTG-3' (SEQ ID NO: 36) |
| W393F | 5'-GATGATTGGTCTCGTCTTCCGCTCCATGGAGCACC-3' (SEQ ID NO: 37) | 5'-GGTGCTCCATGGAGCGGAAGACGAGACCAATCATC-3' (SEQ ID NO: 38) |
| hERα (LBD, 303-ter) | 5'-CATGAATTCAAGAACAGCCTGGCCTTGTCC-3' (SEQ ID NO: 39) | 5'-CATGCTAGCTCAGACCGTGGCAGGGAAACCCTC-3' (SEQ ID NO: 40) |

The expression vector with a His-tag was transformed into Rosetta2(DE3)pLysS E. coli cells (Novagen). For protein expression, E. coli cells were grown in TB medium at 37° C. with 100 µg/ml ampicillin and 34 µg/ml chloramphenicol. When $OD_{600}$ reached 0.4, cell cultures were cooled to 16° C. and protein expression was then induced by the addition of 0.1 mM IPTG in the presence of 10 µM 17β-E2. The cultures were shaken at 16° C. for another 18 h before the cells were harvested by centrifugation. The cells were resuspended in a buffer (referred to as buffer A; 50 mM HEPES (pH 7.5), 300 mM NaCl, 50 mM arginine, 50 mM glutamate, 5 mM β-mercaptoethanol (BME), 5% glycerol, 10 µM estradiol, and 10 µM Zn acetate) supplemented with 20 mM imidazole, 0.1 mg/ml DNase I, and protease inhibitor cocktail (Roche, Indianapolis, Ind.). The cells were disrupted by sonication or using a M110Y microfluidizer (Microfluidics, Newton, Mass.). Cell debris was removed by centrifugation at 18,000×g for 45 min at 4° C. Cleared supernatant was incubated with TALON resin (Clontech). Wash by imidazole step gradients and resin elution by buffer A with 40 mM imidazole was applied. Eluted proteins were incubated with TEV protease at a molar ratio of 1:50 (TEV:protein) and dialyzed into buffer A overnight at 4° C. TEV protease and uncleaved hERα were removed by Talon resin. The protein was subsequently concentrated and purified by HiLoad 16/600 Superdex 200 pg column with an equilibration buffer (referred to as buffer B; 10 mM CHES (pH 9.5), 125 mM NaCl, 5 mM KCl, 4 mM $MgCl_2$, 50 mM arginine, 50 mM glutamate, 5 mM TCEP, 5% glycerol, 10 µm Zn acetate, and 10 µM E2). The 18-bp oligonucleotide with sequences 5'-TAGGTACACGTGACCTGCG-3' (SEQ ID NO: 41)
and
5'-CGCAGGTCACTGTGACCTA-3' (SEQ ID NO: 42)

(Integrated DNA Technologies, Inc) contains a consensus estrogen response element (ERE) as adopted in the DBD crystal structure (PDB entry 1HCQ), was heated to 95° C. and slowly cooled down to ensure the formation of a double-stranded DNA duplex (referred to as ERE-DNA). Eluted hERα proteins were incubated with a 1.2× molar ratio of ERE-DNA and a 3.0× molar ratio of the coactivator TIF2 peptide, KHNALLRYLLDKDD (SEQ ID NO: 43), as adopted in the LBD crystal structure (PDB 1GWR), and placed on ice for 1 h. Final gel filtration purification by a Superdex 200 10/300 GL column (GE) equilibrated with buffer B was performed to obtain the final hERα$^{complex}$ samples.

Hydroxyl Radical Protein Footprinting

Purified hERα$^{complex}$ samples at micromolar concentrations were exposed to a focused synchrotron X-ray white beam for 0-800 ms at the 5.3.1 beamline of Advanced Light Source (Berkeley, Calif.). The samples were quenched, frozen, and later digested with the protease pepsin. The sites of oxidation were detected and analyzed by liquid chromatography-mass spectrometry. Increasing X-ray exposure time results in an increase in modified population and a reduction in unmodified species (see FIG. 9 for representative dose-response plots). The fit to the dose-response plot provides the rate of side chain modification, which is governed by intrinsic reactivity of each amino acid and by the solvent accessibility of the side chain to hydroxyl radicals. The ratio of the intrinsic reactivity and measured footprinting rates yields protection factors (PFs), which are used to directly compare the solvent accessibility for different residues across the protein.

Beam parameters were optimized by using an Alexa-488 fluorophore assay. Samples were dialyzed against a footprinting buffer of 5 mM sodium borate, 50 mM NaCl, and 50 mM KCl, pH 9.5, and the protein concentration was adjusted to 2 µM, followed by exposure of 0-800 ms at ambient temperature, and immediately quenched with 10 mM methionine amide to prevent secondary oxidation. Protein samples were then treated with 10 mM DTT at 56° C. for 45 min and alkylated with 25 mM iodoacetamide at room temperature in the dark for 45 min, and then formic acid was added to a final concentration of 0.5% to adjust the target pH=2. Proteolytic cleavage of the irradiated samples was performed using pepsin (Promega, Inc.) at 37° C. for 3 h at an enzyme-to-protein molar ratio of 1:20. The digestion reaction was terminated by heating at 95° C. for 2 min. Identification and quantification of the sites of radiolytic modification were performed by liquid chromatography-mass spectrometry (LC-MS) analysis of pepsin-digested samples on an Orbitrap Elite mass spectrometer (Thermo Scientific, CA) interfaced with a Waters nanoAcquity UPLC system (Waters, MA). A total of 2 pmol of proteolytic peptides were loaded on a trap column (180 µm×20 mm packed with C18 Symmetry, 5 µm, 100 Å (Waters, MA)) to wash away salts and concentrate peptides. The peptide mixture was eluted on a reverse phase column (75 µm×250 mm column, packed with C18 BEH130, 1.7 µm, 130 Å (Waters, MA)) using a gradient of 2-55% mobile phase B (0.1% formic acid and acetonitrile (ACN)) vs. mobile phase A (100% water/0.1% formic acid) over a period of 60 min at 37° C. with a flow rate of 300 nl/min. The peptides eluted from the reverse phase column were introduced into the nano-electrospray source at a capillary voltage of 2.5 kV. Tandem mass spectrometry (MS/MS) data were acquired in the positive ion mode. In the first MS (MS1) analysis, a full scan was recorded for eluted peptides (m/z range of 350-1600) in the Fourier transform mass analyzer at resolution of 120,000, followed by MS/MS of the 20 most intense peptide ions scanned in the ion trap mass analyzer. Detected ion currents for peptic peptides in MS1 experiments were used to determine the extent of oxidation for each modified site by separate quantification of the unmodified peptides and their radiolytic products, and MS/MS spectra were acquired to identify specific sites of modification. The resulting MS/MS spectra were searched against the hERα$^{CDE}$ protein database using the software MassMatrix with mass accuracy values of 10 ppm and 0.7 Daltons for MS1 and MS/MS scans, respectively, and allowed variable modifications including carbamidomethylation for cysteines and all known oxidative modifications previously documented for amino acid side chains. All MS/MS spectra for reported sites were examined manually and verified individually. The footprinting rate ($k_{fp}$) was derived for each residue lying on individual domain surfaces via a dose-response curve, i.e., the fraction of unmodified residues by hydroxyl radicals as function of X-ray exposure time. Single-residue protection factors (PFs) were subsequently calculated by dividing the intrinsic reactivity of the residue by its $k_{fp}$ value.

Small-Angle X-Ray Scattering

A chromatography-coupled setup was used for SAXS data collection of purified hERα$^{CDE}$ proteins eluted with the ligands of E2, ERE-DNA, and a coactivator TIF2 peptide at the BioCAT-18-ID beamline of the Advanced Photon Source (Argonne, IL). The hERα$^{complex}$ was eluted through a size exclusion column (SEC) equilibrated with saturated ligands. A Superdex 200 10/300 column (GE) at a flow rate of 0.5 ml/min was used in conjunction with an AKTA pure FPLC machine (GE Health Sciences). Scattering images were collected every 3 s along the elution at a flow rate of 0.5 ml/min. Each image was recorded with a 2-s exposure time. A set of six scattering images of the hERα$^{complex}$ near the elution peak were merged and a total of 34 images before and after the peak were used as buffer scattering for buffer subtraction. Data reduction resulted in a final one-dimensional I(q) profile with a bin size of Δq~0.004 Å$^{-1}$. A buffer of 10 mM CHES pH 9.5, 50 mM NaCl, 50 mM KCl, 4 mM MgSO$_4$, 50 mM Arg, 50 mM Glu, 5% glycerol, 1 mM TCEP, and 2 μM E2 was used for size exclusion chromatography. The X-ray energy was 12 keV. Parameters for SEC-SAXS data collection are listed in Table 3, according to the recent SAXS data deposition guideline and practice.

TABLE 3

SEC-SAXS data collection parameters and modeling details

Data collection parameters

| | |
|---|---|
| Experiment date | Aug. 10, 2014 |
| Beamline/Instrument | APS/BioCAT-18-ID, MAR 165 CCD |
| Wavelength | 1.03 Å |
| Beam geometry | 3 μm (V) × 5 μm (H) |
| Photon flux | 1.3 × 10$^{12}$ phs/s |
| Wavelength | 1.03 Å |
| Sample detector distance | 3 m |

TABLE 3-continued

SEC-SAXS data collection parameters and modeling details

| | |
|---|---|
| q range | 0.005-0.3 Å$^{-1}$ |
| Exposure time | 1.1 sec |
| SEC-SAXS column | Superdex 200 GL 10/300 |
| SEC-elution volume | 0.5 μL |
| SEC flow-rate | 0.5 ml/min |
| Sample injection concentration | 3.5 mg/ml |
| Temperature | 10° C. |
| Software for data reduction | Fit2D[1], ATSAS 2.8.4[2] |
| Software for SAXS computing | Fast-SAXS-pro[3] and Crysol[4] |
| Software for structural modeling | In-house iSPOT[5,6] |
| Structural parameters | |
| $R_g$ from Guinier | 38.0 ± 0.3 Å |
| I(0) from Guinier | 4.10 ± 0.04 |
| Molecular mass from I(0) | 99.7 kDa |
| Molecular mass from PDB | 98.3 kDa |
| q-range for Guinier fitting | 0.017-0.033 |
| q $R_g$ (max) | 1.24 |
| Porod Volume | 166828 (Å$^3$) |
| SASBDB ID | SASDDU8 (https://www.sasbdb.org/data/SASDDU8) |

Computational Docking

Docking simulations were based on the crystal structures of the DNA-bound DBD homodimer and the E2-bound LBD homodimer in complex with a coactivator TIF2 peptide by a series of rigid-body docking and coarse-grained modeling, with extensive conformational search, followed by atomic-level molecular dynamics simulations restrained between the DBD packet of Y191/Y195/W200 and the LBD packet of I326/W393/L409. Each docked conformation was evaluated against experimental SAXS and footprinting data via the scoring functions $\chi^2$ (Eq. 1) and $\varphi^2$ (Eq. 2) for the selection of the best-fit ensemble structures of the hERα$^{complex}$.

Crystal structures of the DNA-bound DBD homodimer (PDB entry 1 HCQ) and the E2/peptide-bound LBD homodimer (PDB entries 1QKU and 1GWR) were used in the following three steps. Rigid-body docking of these two domain-homodimers each treated as a separate entity was performed to generate an initial set of 3125 poses that uniformly cover the interdimer rotational degrees of freedom. Coarse-grained (CG) Langevin simulations were implemented for each pose to extensively sample the translational motion between the centers of mass of the two dimers with a distance range of 25-50 Å, for a total of 390,625 ns. Final atomic-level structure reconstruction was performed by aligning the crystal structures of the two domain-dimers onto the CG structures for those with a center-of-mass distance of <20 Å between the clusters of footprinting-detected residues Y191/Y195/W200 and I326/W393/L409. The domain-connecting hinge was built using the loop modeling software Jackal. Restrained simulations were performed using Amber165, whereas the LBD homodimer was position restrained and the DBD homodimer was RMSD restrained both at their Cα and Cβ atoms with a harmonic spring constant of 10.0 kcal/mol/Å$^2$. To arrive at a set of 176 final conformations with the lowest $\chi^2$ (Eq. 1) and $\varphi^2$ (Eq. 2), the center-of-mass distance of the Cγ atoms was linearly restrained between the two clusters of residues (Y191/Y195/W200 and I326/W393/L409) with a target distance moving from 10 to 2 Å over a period of 1.0 ns and a force constant of 20 kcal/mol/Å$^2$.

The molecular force fields of amber-ff14SB, TIP3P, and DNA.OL15 were used for all-atom, explicit-solvent simulations, and the parameters for the estradiol E2 were generated using the software package antechamber. The system was placed in a rectangle water box with a buffer distance of 10 Å in the presence of a 150-mM salt solution. Standard periodic boundary conditions were applied with a non-bond cutoff of 12 Å. Simulations were performed at a temperature of 300 K and a pressure of 1 atm with a 2-fs time step.

Transient Transfection Reporter Assay

Wild-type and mutant hERα-LBD (residues 303-595) were subcloned with Gal4-DBD to generate a Gal4-DBD/hERα-LBD fusion construct. The sequences of primers for cloning and mutagenic sequences are shown in Table 2. The effects of ERα mutations on transcription activity were evaluated by transient transfection reporter assays using a dual luciferase reporter assay. HeLa cells were co-transfected with an HA-hERα or a Gal4-DBD/hERα-LBD expression plasmid (2 μg) on 60-mm plate and an ERE-TK-Luc or Gal4-TK-Luc (2.5 μg) and Renilla-Luc (0.5 μg). Cells were then split to a 24-well plate and starved at 2% FBS in DMEM medium. After overnight starvation, medium was replaced with or without 100 nM E2 (Cayman #10006315). Twelve hours later, cells were harvested and firefly luciferase (FLuc) and renilla-luciferase (RLuc) activities were measured using dual luciferase reporter assay kit (Promega, E1910) according to the manufacturer's protocol. An aliquot of lysates was subject to western blotting to visualize the expression of wild-type and mutant hERα, where western blottings were performed using anti-HA (1:1000, sc-805, Santa Cruz), anti-Gal4 (1:2000, sc-729, Santa Cruz), and anti-β-actin (1:1000, A5441, Sigma-Aldrich) antibodies. Briefly, 50 μl of lysate was mixed with 50 μl of Luciferase Assay Reagent II to determine luminescent signal for FLuc. After the luminescence was quantified, the FLuc activity was quenched and RLuc activity was measured by adding 5 μl Stop & Glo Reagent (E1910 Promega). Luciferase activity was normalized to the level of RLuc activity. Each reaction was performed in triplicate, and triplicates were averaged prior to statistical analysis.

Genetically Engineered hERα-Specific Fluorescence Assay

Four out of all five tryptophan residues (W292, W360, W383, and W393) in the hERα$^{complex}$ were mutated to phenylalanine except W200, which was kept as an intrinsic fluorescence probe. The emission spectra of hERα$^{complex}$/W200 were recorded between 310 and 400 nm with a bandwidth of 5 nm at 25° C. using a FluoroMax-3 spectrofluorometer (Horiba Scientific). Buffer correction was applied to all samples at a protein concentration of 0.1 mg/ml. Excitation at 295 nm was used to minimize the influence from tyrosine.

Fluorescence Anisotropy DNA-Binding Assay

The fluorescence-conjugated double-strand ERE-DNA was prepared by annealing 6-FAM (6-carboxyfluorescein) 5'-labeled strands (5'-TAGGTCACAGTGACCTGCG-3' (SEQ ID NO: 44) and 5'-CGCAGGTCACTGTGACCTA-3' (SEQ ID NO: 45); IDT, Inc) in a buffer containing 10 mM CHES (pH 9.5), 50 mM KCl, 50 mM NaCl, 4 mM MgCl$_2$, 50 mM arginine, 50 mM glutamic acid, 5 mM TCEP, 5% glycerol with 10 μM ZnCl$_2$, and 10 μM E2. The resulting 20 nM ERE-DNA was incubated with purified proteins in the presence of E2 and coactivator peptides for 10 min for the binding assay and loaded into a 96-well plate (Greiner Bio-one). Fluorescence anisotropy intensity was recorded at a series of hERα$^{CDE}$ protein concentrations using a Tecan M1000-PRO microplate reader.

Surface Plasmon Resonance

Peptide binding between the hERα$^{CDE}$ and a coactivator TIF2 peptide (KENALLRYLLDKDD) (SEQ ID NO: 46) was measured by surface plasmon resonance (SPR) using a Biacore T100 system (GE Healthcare). Sensorgrams were recorded for a concentration series of the hERα$^{CDE}$-DNA-E2 complex, where the biotinylated TIF2 peptide (captured at 10 RUs) was immobilized on an SA sensor chip (GE Healthcare) and a flow rate of 20 μl/min of the complex at a concentration range of 0-5 μM was used for injection over the peptide-binding surface. Measurements were conducted at 25° C. using a Biacore T100 system.

All patent applications, patents, and printed publications cited herein are incorporated herein by reference in the entireties, except for any definitions, subject matter disclaimers or disavowals, and except to the extent that the incorporated material is inconsistent with the express disclosure herein, in which case the language in this disclosure controls.

What is claimed is:

1. An isolated mutant human estrogen receptor alpha (hERα) comprising a DNA-binding domain (DBD), a ligand-binding domain (LBD), and an interface between the DBD and the LBD, wherein the tryptophan residue W200 is not mutated to a phenylalanine residue, and wherein at least three tryptophan residues selected from W292, W360, W383, and W393 are mutated to a phenylalanine residue.

2. The isolated mutant hERα of claim 1, wherein only three tryptophan residues selected from W292, W360, W383, and W393 are mutated to phenylalanine residues.

3. The isolated mutant hERα of claim 1, wherein all four tryptophan residues W292, W360, W383, and W393 are mutated to phenylalanine residues.

4. The isolated mutant hERα of claim 1, wherein the mutant further comprises amino acid residues 181-552 of hERα.

5. A kit comprising a mutant human estrogen receptor alpha (hERα) comprising a DNA-binding domain (DBD), a ligand-binding domain (LBD), and an interface between the DBD and the LBD, wherein the tryptophan residue W200 is not mutated to a phenylalanine residue, and wherein at least three tryptophan residues selected from W292, W360, W383, and W393 are mutated to a phenylalanine residue;
    at least one protein buffer; and
    instructions for using the kit to carry out a method of drug discovery.

6. The kit of claim 5, wherein the protein buffer comprises one or more of CHES, KCl, NaCl, MgCl$_2$, arginine, glutamic acid, TCEP, glycerol, and ZnCl.

7. The kit of claim 5, wherein the protein buffer comprises a drug that can bind to the estrogen receptor.

8. The kit of claim 5, wherein the protein buffer comprises estradiol.

9. The kit of claim 5, wherein only three tryptophan residues selected from W292, W360, W383, and W393 are mutated to phenylalanine residues.

10. The kit of claim 5, wherein all four mutated tryptophan residues W292, W360, W383, and W393 are mutated to phenylalanine residues.

* * * * *

SEQUENCE LISTING

<160> NUMBER OF SEQ ID NOS: 46

<210> SEQ ID NO 1
<211> LENGTH: 372
<212> TYPE: PRT
<213> ORGANISM: Homo sapiens

<400> SEQUENCE: 1

```
Glu Thr Arg Tyr Cys Ala Val Cys Asn Asp Tyr Ala Ser Gly Tyr His
1               5                   10                  15

Tyr Gly Val Trp Ser Cys Glu Gly Cys Lys Ala Phe Phe Lys Arg Ser
            20                  25                  30

Ile Gln Gly His Asn Asp Tyr Met Cys Pro Ala Thr Asn Gln Cys Thr
        35                  40                  45

Ile Asp Lys Asn Arg Arg Lys Ser Cys Gln Ala Cys Arg Leu Arg Lys
    50                  55                  60

Cys Tyr Glu Val Gly Met Met Lys Gly Gly Ile Arg Lys Asp Arg Arg
65                  70                  75                  80

Gly Gly Arg Met Leu Lys His Lys Arg Gln Arg Asp Asp Gly Glu Gly
                85                  90                  95
```

Arg Gly Glu Val Gly Ser Ala Gly Asp Met Arg Ala Ala Asn Leu Trp
            100                 105                 110

Pro Ser Pro Leu Met Ile Lys Arg Ser Lys Lys Asn Ser Leu Ala Leu
            115                 120                 125

Ser Leu Thr Ala Asp Gln Met Val Ser Ala Leu Leu Asp Ala Glu Pro
        130                 135                 140

Pro Ile Leu Tyr Ser Glu Tyr Asp Pro Thr Arg Pro Phe Ser Glu Ala
145                 150                 155                 160

Ser Met Met Gly Leu Leu Thr Asn Leu Ala Asp Arg Glu Leu Val His
                165                 170                 175

Met Ile Asn Trp Ala Lys Arg Val Pro Gly Phe Val Asp Leu Thr Leu
            180                 185                 190

His Asp Gln Val His Leu Leu Glu Cys Ala Trp Leu Glu Ile Leu Met
        195                 200                 205

Ile Gly Leu Val Trp Arg Ser Met Glu His Pro Gly Lys Leu Leu Phe
    210                 215                 220

Ala Pro Asn Leu Leu Leu Asp Arg Asn Gln Gly Lys Cys Val Glu Gly
225                 230                 235                 240

Met Val Glu Ile Phe Asp Met Leu Leu Ala Thr Ser Ser Arg Phe Arg
                245                 250                 255

Met Met Asn Leu Gln Gly Glu Glu Phe Val Cys Leu Lys Ser Ile Ile
            260                 265                 270

Leu Leu Asn Ser Gly Val Tyr Thr Phe Leu Ser Ser Thr Leu Lys Ser
        275                 280                 285

Leu Glu Glu Lys Asp His Ile His Arg Val Leu Asp Lys Ile Thr Asp
    290                 295                 300

Thr Leu Ile His Leu Met Ala Lys Ala Gly Leu Thr Leu Gln Gln Gln
305                 310                 315                 320

His Gln Arg Leu Ala Gln Leu Leu Leu Ile Leu Ser His Ile Arg His
                325                 330                 335

Met Ser Asn Lys Gly Met Glu His Leu Tyr Ser Met Lys Cys Lys Asn
            340                 345                 350

Val Val Pro Leu Tyr Asp Leu Leu Leu Glu Met Leu Asp Ala His Arg
        355                 360                 365

Leu His Ala Pro
    370

<210> SEQ ID NO 2
<211> LENGTH: 14
<212> TYPE: PRT
<213> ORGANISM: Homo sapiens

<400> SEQUENCE: 2

Lys Glu Asn Ala Leu Leu Arg Tyr Leu Leu Asp Lys Asp Asp
1               5                   10

<210> SEQ ID NO 3
<211> LENGTH: 14
<212> TYPE: PRT
<213> ORGANISM: Homo sapiens

<400> SEQUENCE: 3

Lys Glu Asn Ala Leu Leu Arg Tyr Leu Leu Asp Lys Asp Asp
1               5                   10

<210> SEQ ID NO 4

-continued

```
<211> LENGTH: 595
<212> TYPE: PRT
<213> ORGANISM: Homo sapiens

<400> SEQUENCE: 4

Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Ile Pro Leu Glu Arg Pro Leu Gly Glu Val Tyr Leu Asp Ser Ser Lys
        35                  40                  45

Pro Ala Val Tyr Asn Tyr Pro Glu Gly Ala Ala Tyr Glu Phe Asn Ala
    50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His
            100                 105                 110

Pro Pro Pro Gln Leu Ser Pro Phe Leu Gln Pro His Gly Gln Gln Val
        115                 120                 125

Pro Tyr Tyr Leu Glu Asn Glu Pro Ser Gly Tyr Thr Val Arg Glu Ala
    130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
        195                 200                 205

Phe Lys Arg Ser Ile Gln Gly His Asn Asp Tyr Met Cys Pro Ala Thr
    210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
            260                 265                 270

Asp Gly Glu Gly Arg Gly Glu Val Gly Ser Ala Gly Asp Met Arg Ala
        275                 280                 285

Ala Asn Leu Trp Pro Ser Pro Leu Met Ile Lys Arg Ser Lys Lys Asn
    290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
        355                 360                 365

Asp Leu Thr Leu His Asp Gln Val His Leu Leu Glu Cys Ala Trp Leu
    370                 375                 380

Glu Ile Leu Met Ile Gly Leu Val Trp Arg Ser Met Glu His Pro Gly
```

```
                385                 390                 395                 400
Lys Leu Leu Phe Ala Pro Asn Leu Leu Asp Arg Asn Gln Gly Lys
                    405                 410                 415

Cys Val Glu Gly Met Val Glu Ile Phe Asp Met Leu Leu Ala Thr Ser
                420                 425                 430

Ser Arg Phe Arg Met Met Asn Leu Gln Gly Glu Glu Phe Val Cys Leu
            435                 440                 445

Lys Ser Ile Ile Leu Leu Asn Ser Gly Val Tyr Thr Phe Leu Ser Ser
        450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                    485                 490                 495

Leu Gln Gln Gln His Gln Arg Leu Ala Gln Leu Leu Leu Ile Leu Ser
                500                 505                 510

His Ile Arg His Met Ser Asn Lys Gly Met Glu His Leu Tyr Ser Met
            515                 520                 525

Lys Cys Lys Asn Val Val Pro Leu Tyr Asp Leu Leu Leu Glu Met Leu
        530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                    565                 570                 575

His Ser Leu Gln Lys Tyr Tyr Ile Thr Gly Glu Ala Glu Gly Phe Pro
                580                 585                 590

Ala Thr Val
        595

<210> SEQ ID NO 5
<211> LENGTH: 82
<212> TYPE: PRT
<213> ORGANISM: Homo sapiens

<400> SEQUENCE: 5

Glu Thr Arg Tyr Cys Ala Val Cys Asn Asp Tyr Ala Ser Gly Tyr His
1               5                   10                  15

Tyr Gly Val Trp Ser Cys Glu Gly Cys Lys Ala Phe Phe Lys Arg Ser
            20                  25                  30

Ile Gln Gly His Asn Asp Tyr Met Cys Pro Ala Thr Asn Gln Cys Thr
        35                  40                  45

Ile Asp Lys Asn Arg Arg Lys Ser Cys Gln Ala Cys Arg Leu Arg Lys
    50                  55                  60

Cys Tyr Glu Val Gly Met Met Lys Gly Gly Ile Arg Lys Asp Arg Arg
65                  70                  75                  80

Gly Gly

<210> SEQ ID NO 6
<211> LENGTH: 259
<212> TYPE: PRT
<213> ORGANISM: Homo sapiens

<400> SEQUENCE: 6

Met Asp Pro Met Ile Lys Arg Ser Lys Lys Asn Ser Leu Ala Leu Ser
1               5                   10                  15

Leu Thr Ala Asp Gln Met Val Ser Ala Leu Leu Asp Ala Glu Pro Pro
            20                  25                  30
```

```
Ile Leu Tyr Ser Glu Tyr Asp Pro Thr Arg Pro Phe Ser Glu Ala Ser
        35                  40                  45

Met Met Gly Leu Leu Thr Asn Leu Ala Asp Arg Glu Leu Val His Met
 50                  55                  60

Ile Asn Trp Ala Lys Arg Val Pro Gly Phe Val Asp Leu Thr Leu His
 65                  70                  75                  80

Asp Gln Val His Leu Leu Glu Cys Ala Trp Leu Glu Ile Leu Met Ile
                 85                  90                  95

Gly Leu Val Trp Arg Ser Met Glu His Pro Gly Lys Leu Leu Phe Ala
                100                 105                 110

Pro Asn Leu Leu Leu Asp Arg Asn Gln Gly Lys Cys Val Glu Gly Met
                115                 120                 125

Val Glu Ile Phe Asp Met Leu Leu Ala Thr Ser Ser Arg Phe Arg Met
        130                 135                 140

Met Asn Leu Gln Gly Glu Glu Phe Val Cys Leu Lys Ser Ile Ile Leu
145                 150                 155                 160

Leu Asn Ser Gly Val Tyr Thr Phe Leu Ser Ser Thr Leu Lys Ser Leu
                165                 170                 175

Glu Glu Lys Asp His Ile His Arg Val Leu Asp Lys Ile Thr Asp Thr
                180                 185                 190

Leu Ile His Leu Met Ala Lys Ala Gly Leu Thr Leu Gln Gln Gln His
        195                 200                 205

Gln Arg Leu Ala Gln Leu Leu Leu Ile Leu Ser His Ile Arg His Met
        210                 215                 220

Ser Asn Lys Gly Met Glu His Leu Tyr Ser Met Lys Cys Lys Asn Val
225                 230                 235                 240

Val Pro Leu Tyr Asp Leu Leu Leu Glu Met Leu Asp Ala His Arg Leu
                245                 250                 255

His Ala Pro

<210> SEQ ID NO 7
<211> LENGTH: 372
<212> TYPE: PRT
<213> ORGANISM: Homo sapiens

<400> SEQUENCE: 7

Glu Thr Arg Tyr Cys Ala Val Cys Asn Asp Tyr Ala Ser Gly Tyr His
 1               5                  10                  15

Tyr Gly Val Trp Ser Cys Glu Gly Cys Lys Ala Phe Phe Lys Arg Ser
                 20                  25                  30

Ile Gln Gly His Asn Asp Tyr Met Cys Pro Ala Thr Asn Gln Cys Thr
        35                  40                  45

Ile Asp Lys Asn Arg Arg Lys Ser Cys Gln Ala Cys Arg Leu Arg Lys
     50                  55                  60

Cys Tyr Glu Val Gly Met Met Lys Gly Gly Ile Arg Lys Asp Arg Arg
 65                  70                  75                  80

Gly Gly Arg Met Leu Lys His Lys Arg Gln Arg Asp Asp Gly Glu Gly
                 85                  90                  95

Arg Gly Glu Val Gly Ser Ala Gly Asp Met Arg Ala Ala Asn Leu Trp
                100                 105                 110

Pro Ser Pro Leu Met Ile Lys Arg Ser Lys Lys Asn Ser Leu Ala Leu
                115                 120                 125

Ser Leu Thr Ala Asp Gln Met Val Ser Ala Leu Leu Asp Ala Glu Pro
        130                 135                 140
```

Pro Ile Leu Tyr Ser Glu Tyr Asp Pro Thr Arg Pro Phe Ser Glu Ala
145                 150                 155                 160

Ser Met Met Gly Leu Leu Thr Asn Leu Ala Asp Arg Glu Leu Val His
            165                 170                 175

Met Ile Asn Trp Ala Lys Arg Val Pro Gly Phe Val Asp Leu Thr Leu
        180                 185                 190

His Asp Gln Val His Leu Leu Glu Cys Ala Trp Leu Glu Ile Leu Met
    195                 200                 205

Ile Gly Leu Val Trp Arg Ser Met Glu His Pro Gly Lys Leu Leu Phe
210                 215                 220

Ala Pro Asn Leu Leu Leu Asp Arg Asn Gln Gly Lys Cys Val Glu Gly
225                 230                 235                 240

Met Val Glu Ile Phe Asp Met Leu Leu Ala Thr Ser Ser Arg Phe Arg
                245                 250                 255

Met Met Asn Leu Gln Gly Glu Glu Phe Val Cys Leu Lys Ser Ile Ile
            260                 265                 270

Leu Leu Asn Ser Gly Val Tyr Thr Phe Leu Ser Ser Thr Leu Lys Ser
        275                 280                 285

Leu Glu Glu Lys Asp His Ile His Arg Val Leu Asp Lys Ile Thr Asp
    290                 295                 300

Thr Leu Ile His Leu Met Ala Lys Ala Gly Leu Thr Leu Gln Gln Gln
305                 310                 315                 320

His Gln Arg Leu Ala Gln Leu Leu Leu Ile Leu Ser His Ile Arg His
                325                 330                 335

Met Ser Asn Lys Gly Met Glu His Leu Tyr Ser Met Lys Cys Lys Asn
            340                 345                 350

Val Val Pro Leu Tyr Asp Leu Leu Leu Glu Met Leu Asp Ala His Arg
        355                 360                 365

Leu His Ala Pro
    370

<210> SEQ ID NO 8
<211> LENGTH: 415
<212> TYPE: PRT
<213> ORGANISM: Homo sapiens

<400> SEQUENCE: 8

Glu Thr Arg Tyr Cys Ala Val Cys Asn Asp Tyr Ala Ser Gly Tyr His
1               5                   10                  15

Tyr Gly Val Trp Ser Cys Glu Gly Cys Lys Ala Phe Phe Lys Arg Ser
            20                  25                  30

Ile Gln Gly His Asn Asp Tyr Met Cys Pro Ala Thr Asn Gln Cys Thr
        35                  40                  45

Ile Asp Lys Asn Arg Arg Lys Ser Cys Gln Ala Cys Arg Leu Arg Lys
    50                  55                  60

Cys Tyr Glu Val Gly Met Met Lys Gly Gly Ile Arg Lys Asp Arg Arg
65                  70                  75                  80

Gly Gly Arg Met Leu Lys His Lys Arg Gln Arg Asp Asp Gly Glu Gly
                85                  90                  95

Arg Gly Glu Val Gly Ser Ala Gly Asp Met Arg Ala Ala Asn Leu Trp
            100                 105                 110

Pro Ser Pro Leu Met Ile Lys Arg Ser Lys Lys Asn Ser Leu Ala Leu
        115                 120                 125

Ser Leu Thr Ala Asp Gln Met Val Ser Ala Leu Leu Asp Ala Glu Pro

Pro Ile Leu Tyr Ser Glu Tyr Asp Pro Thr Arg Pro Phe Ser Glu Ala
145                 150                 155                 160

Ser Met Met Gly Leu Leu Thr Asn Leu Ala Asp Arg Glu Leu Val His
            165                 170                 175

Met Ile Asn Trp Ala Lys Arg Val Pro Gly Phe Val Asp Leu Thr Leu
        180                 185                 190

His Asp Gln Val His Leu Leu Glu Cys Ala Trp Leu Glu Ile Leu Met
    195                 200                 205

Ile Gly Leu Val Trp Arg Ser Met Glu His Pro Gly Lys Leu Leu Phe
210                 215                 220

Ala Pro Asn Leu Leu Leu Asp Arg Asn Gln Gly Lys Cys Val Glu Gly
225                 230                 235                 240

Met Val Glu Ile Phe Asp Met Leu Leu Ala Thr Ser Ser Arg Phe Arg
            245                 250                 255

Met Met Asn Leu Gln Gly Glu Glu Phe Val Cys Leu Lys Ser Ile Ile
        260                 265                 270

Leu Leu Asn Ser Gly Val Tyr Thr Phe Leu Ser Ser Thr Leu Lys Ser
    275                 280                 285

Leu Glu Glu Lys Asp His Ile His Arg Val Leu Asp Lys Ile Thr Asp
290                 295                 300

Thr Leu Ile His Leu Met Ala Lys Ala Gly Leu Thr Leu Gln Gln Gln
305                 310                 315                 320

His Gln Arg Leu Ala Gln Leu Leu Leu Ile Leu Ser His Ile Arg His
            325                 330                 335

Met Ser Asn Lys Gly Met Glu His Leu Tyr Ser Met Lys Cys Lys Asn
        340                 345                 350

Val Val Pro Leu Tyr Asp Leu Leu Leu Glu Met Leu Asp Ala His Arg
    355                 360                 365

Leu His Ala Pro Thr Ser Arg Gly Gly Ala Ser Val Glu Glu Thr Asp
370                 375                 380

Gln Ser His Leu Ala Thr Ala Gly Ser Thr Ser Ser His Ser Leu Gln
385                 390                 395                 400

Lys Tyr Tyr Ile Thr Gly Glu Ala Glu Gly Phe Pro Ala Thr Val
            405                 410                 415

<210> SEQ ID NO 9
<211> LENGTH: 372
<212> TYPE: PRT
<213> ORGANISM: Homo sapiens

<400> SEQUENCE: 9

Glu Thr Arg Tyr Cys Ala Val Cys Asn Asp Tyr Ala Ser Gly Tyr His
1               5                   10                  15

Tyr Gly Val Trp Ser Cys Glu Gly Cys Lys Ala Phe Phe Lys Arg Ser
            20                  25                  30

Ile Gln Gly His Asn Asp Tyr Met Cys Pro Ala Thr Asn Gln Cys Thr
        35                  40                  45

Ile Asp Lys Asn Arg Arg Lys Ser Cys Gln Ala Cys Arg Leu Arg Lys
    50                  55                  60

Cys Tyr Glu Val Gly Met Met Lys Gly Gly Ile Arg Lys Asp Arg Arg
65                  70                  75                  80

Gly Gly Arg Met Leu Lys His Lys Arg Gln Arg Asp Asp Gly Glu Gly
            85                  90                  95

Arg Gly Glu Val Gly Ser Ala Gly Asp Met Arg Ala Ala Asn Leu Trp
            100                 105                 110

Pro Ser Pro Leu Met Ile Lys Arg Ser Lys Asn Ser Leu Ala Leu
        115                 120                 125

Ser Leu Thr Ala Asp Gln Met Val Ser Ala Leu Leu Asp Ala Glu Pro
    130                 135                 140

Pro Ile Leu Tyr Ser Glu Tyr Asp Pro Thr Arg Pro Phe Ser Glu Ala
145                 150                 155                 160

Ser Met Met Gly Leu Leu Thr Asn Leu Ala Asp Arg Glu Leu Val His
                165                 170                 175

Met Ile Asn Trp Ala Lys Arg Val Pro Gly Phe Val Asp Leu Thr Leu
            180                 185                 190

His Asp Gln Val His Leu Leu Glu Cys Ala Trp Leu Glu Ile Leu Met
        195                 200                 205

Ile Gly Leu Val Trp Arg Ser Met Glu His Pro Gly Lys Leu Leu Phe
    210                 215                 220

Ala Pro Asn Leu Leu Asp Arg Asn Gln Gly Lys Cys Val Glu Gly
225                 230                 235                 240

Met Val Glu Ile Phe Asp Met Leu Leu Ala Thr Ser Ser Arg Phe Arg
            245                 250                 255

Met Met Asn Leu Gln Gly Glu Glu Phe Val Cys Leu Lys Ser Ile Ile
        260                 265                 270

Leu Leu Asn Ser Gly Val Tyr Thr Phe Leu Ser Ser Thr Leu Lys Ser
    275                 280                 285

Leu Glu Glu Lys Asp His Ile His Arg Val Leu Asp Lys Ile Thr Asp
290                 295                 300

Thr Leu Ile His Leu Met Ala Lys Ala Gly Leu Thr Leu Gln Gln Gln
305                 310                 315                 320

His Gln Arg Leu Ala Gln Leu Leu Leu Ile Leu Ser His Ile Arg His
            325                 330                 335

Met Ser Asn Lys Gly Met Glu His Leu Tyr Ser Met Lys Cys Lys Asn
        340                 345                 350

Val Val Pro Leu Tyr Asp Leu Leu Leu Glu Met Leu Asp Ala His Arg
    355                 360                 365

Leu His Ala Pro
    370

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
taggtacacg tgacctgcg                                                19

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
cgcaggtcac tgtgaccta                                                19

```
<210> SEQ ID NO 12
<211> LENGTH: 14
<212> TYPE: PRT
<213> ORGANISM: Homo sapiens

<400> SEQUENCE: 12

Lys Glu Asn Ala Leu Leu Arg Tyr Leu Leu Asp Lys Asp Asp
1               5                   10

<210> SEQ ID NO 13
<211> LENGTH: 372
<212> TYPE: PRT
<213> ORGANISM: Homo sapiens

<400> SEQUENCE: 13

Glu Thr Arg Tyr Cys Ala Val Cys Asn Asp Tyr Ala Ser Gly Tyr His
1               5                   10                  15

Tyr Gly Val Trp Ser Cys Glu Gly Cys Lys Ala Phe Phe Lys Arg Ser
            20                  25                  30

Ile Gln Gly His Asn Asp Tyr Met Cys Pro Ala Thr Asn Gln Cys Thr
        35                  40                  45

Ile Asp Lys Asn Arg Arg Lys Ser Cys Gln Ala Cys Arg Leu Arg Lys
    50                  55                  60

Cys Tyr Glu Val Gly Met Met Lys Gly Gly Ile Arg Lys Asp Arg Arg
65                  70                  75                  80

Gly Gly Arg Met Leu Lys His Lys Arg Gln Arg Asp Asp Gly Glu Gly
                85                  90                  95

Arg Gly Glu Val Gly Ser Ala Gly Asp Met Arg Ala Ala Asn Leu Trp
            100                 105                 110

Pro Ser Pro Leu Met Ile Lys Arg Ser Lys Lys Asn Ser Leu Ala Leu
        115                 120                 125

Ser Leu Thr Ala Asp Gln Met Val Ser Ala Leu Leu Asp Ala Glu Pro
    130                 135                 140

Pro Ile Leu Tyr Ser Glu Tyr Asp Pro Thr Arg Pro Phe Ser Glu Ala
145                 150                 155                 160

Ser Met Met Gly Leu Leu Thr Asn Leu Ala Asp Arg Glu Leu Val His
                165                 170                 175

Met Ile Asn Trp Ala Lys Arg Val Pro Gly Phe Val Asp Leu Thr Leu
            180                 185                 190

His Asp Gln Val His Leu Leu Glu Cys Ala Trp Leu Glu Ile Leu Met
        195                 200                 205

Ile Gly Leu Val Trp Arg Ser Met Glu His Pro Gly Lys Leu Leu Phe
    210                 215                 220

Ala Pro Asn Leu Leu Leu Asp Arg Asn Gln Gly Lys Cys Val Glu Gly
225                 230                 235                 240

Met Val Glu Ile Phe Asp Met Leu Leu Ala Thr Ser Ser Arg Phe Arg
                245                 250                 255

Met Met Asn Leu Gln Gly Glu Glu Phe Val Cys Leu Lys Ser Ile Ile
            260                 265                 270

Leu Leu Asn Ser Gly Val Tyr Thr Phe Leu Ser Ser Thr Leu Lys Ser
        275                 280                 285

Leu Glu Glu Lys Asp His Ile His Arg Val Leu Asp Lys Ile Thr Asp
    290                 295                 300

Thr Leu Ile His Leu Met Ala Lys Ala Gly Leu Thr Leu Gln Gln Gln
305                 310                 315                 320
```

His Gln Arg Leu Ala Gln Leu Leu Ile Leu Ser His Ile Arg His
            325                 330                 335

Met Ser Asn Lys Gly Met Glu His Leu Tyr Ser Met Lys Cys Lys Asn
        340                 345                 350

Val Val Pro Leu Tyr Asp Leu Leu Leu Glu Met Leu Asp Ala His Arg
    355                 360                 365

Leu His Ala Pro
    370

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
taggtacacg tgacctgcg                                                19

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
cgcaggtcac tgtgaccta                                                19

<210> SEQ ID NO 16
<211> LENGTH: 14
<212> TYPE: PRT
<213> ORGANISM: Homo sapiens

<400> SEQUENCE: 16

Lys Glu Asn Ala Leu Leu Arg Tyr Leu Leu Asp Lys Asp Asp
1               5                   10

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ggtgaattcg agactcgcta ctgtgc                                        26

<210> SEQ ID NO 18
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
attggatcct cagggcgcat ggatgg                                        26

<210> SEQ ID NO 19
<211> LENGTH: 39

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gtgcagtgtg caatgaccat gcttcaggct accattatg                              39

<210> SEQ ID NO 20
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gacataatgg tagcctgaag catggtcatt gcacactgca c                           41

<210> SEQ ID NO 21
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ttggatgctg agccccccgc actctattcc gagtatgat                              39

<210> SEQ ID NO 22
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
atcatactcg gaatagagtg cggggggctc agcatccaa                              39

<210> SEQ ID NO 23
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gctgagcccc ccatactcgc ttccgagtat gatcctacc                              39

<210> SEQ ID NO 24
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ggtaggatca tactcggaag cgagtatggg gggctcagc                              39

<210> SEQ ID NO 25
<211> LENGTH: 39
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 25
gtgaagctac tgtttgctgc taacttgctc ttggacagg                               39

<210> SEQ ID NO 26
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cctgtccaag agcaagttag cagcaaacag tagcttcac                               39

<210> SEQ ID NO 27
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
aagctactgt ttgctcctgc cttgctcttg gacaggaac                               39

<210> SEQ ID NO 28
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gttcctgtcc aagagcaagg caggagcaaa cagtagctt                               39

<210> SEQ ID NO 29
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ctgtttgctc ctaacttggc cttggacagg aaccaggga                               39

<210> SEQ ID NO 30
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tccctggttc ctgtccaagg ccaagttagg agcaaacag                               39

<210> SEQ ID NO 31
<211> LENGTH: 32
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 31
gagctgccaa ccttttccca agcccgctca tg                                    32

<210> SEQ ID NO 32
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
catgagcggg cttgggaaaa ggttggcagc tc                                    32

<210> SEQ ID NO 33
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ggttcacatg atcaacttcg cgaagagggt gccag                                 35

<210> SEQ ID NO 34
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ctggcaccct cttcgcgaag ttgatcatgt gaacc                                 35

<210> SEQ ID NO 35
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
caccttctag aatgtgcctt cctagagatc ctgatgattg                            40

<210> SEQ ID NO 36
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
caatcatcag gatctctagg aaggcacatt ctagaaggtg                            40

<210> SEQ ID NO 37
<211> LENGTH: 35
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 37
gatgattggt ctcgtcttcc gctccatgga gcacc                                35

<210> SEQ ID NO 38
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ggtgctccat ggagcggaag acgagaccaa tcatc                                35

<210> SEQ ID NO 39
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
catgaattca agaacagcct ggccttgtcc                                      30

<210> SEQ ID NO 40
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
catgctagct cagaccgtgg cagggaaacc ctc                                  33

<210> SEQ ID NO 41
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
taggtacacg tgacctgcg                                                  19

<210> SEQ ID NO 42
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
cgcaggtcac tgtgaccta                                                  19

<210> SEQ ID NO 43
<211> LENGTH: 14
<212> TYPE: PRT
<213> ORGANISM: Homo sapiens

<400> SEQUENCE: 43
```

```
Lys His Asn Ala Leu Leu Arg Tyr Leu Leu Asp Lys Asp Asp
1               5                   10

<210> SEQ ID NO 44
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
taggtcacag tgacctgcg                                                 19

<210> SEQ ID NO 45
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
cgcaggtcac tgtgaccta                                                 19

<210> SEQ ID NO 46
<211> LENGTH: 14
<212> TYPE: PRT
<213> ORGANISM: Homo sapiens

<400> SEQUENCE: 46

Lys Glu Asn Ala Leu Leu Arg Tyr Leu Leu Asp Lys Asp Asp
1               5                   10
```